(12) United States Patent
Haque et al.

(10) Patent No.: US 12,411,236 B2
(45) Date of Patent: Sep. 9, 2025

(54) IMAGING DEVICES WITH SELECTIVELY ALTERABLE CHARACTERISTICS

(71) Applicant: Exo Imaging, Inc., Santa Clara, CA (US)

(72) Inventors: Yusuf S. Haque, Woodside, CA (US); Sandeep Akkaraju, Wellesley, MA (US); Janusz Bryzek, Santa Clara, CA (US); Larry Skrenes, Hartland, WI (US)

(73) Assignee: Exo Imaging, Inc., Santa Clara, CA (US)

( * ) Notice: Subject to any disclaimer, the term of this patent is extended or adjusted under 35 U.S.C. 154(b) by 0 days.

(21) Appl. No.: 18/649,885

(22) Filed: Apr. 29, 2024

(65) Prior Publication Data

US 2024/0280696 A1 Aug. 22, 2024

Related U.S. Application Data

(62) Division of application No. 17/257,175, filed as application No. PCT/US2019/051328 on Sep. 16, 2019, now Pat. No. 11,971,477.

(Continued)

(51) Int. Cl.
*G01S 15/89* (2006.01)
*A61B 5/00* (2006.01)
(Continued)

(52) U.S. Cl.
CPC ........ *G01S 15/8934* (2013.01); *G01S 15/895* (2013.01); *A61B 5/0095* (2013.01);
(Continued)

(58) Field of Classification Search
CPC . G01S 15/8934; G01S 15/895; A61B 5/0095; A61B 8/06; A61B 8/145;
(Continued)

(56) References Cited

U.S. PATENT DOCUMENTS 4,211,949 A * 7/1980 Brisken .................. G10K 11/02
73/644
4,281,298 A * 7/1981 Gounji ..................... H03H 9/24
219/535

(Continued)

FOREIGN PATENT DOCUMENTS

CA 3105459 A1 * 4/2020 ........... A61B 5/0095
CA 3212626 A1 * 9/2022 ........... G01S 15/892
(Continued)

*Primary Examiner* — Daniel Pihulic
(74) *Attorney, Agent, or Firm* — Morgan, Lewis & Bockius LLP

(57) ABSTRACT

In one example in accordance with the present disclosure, an imaging device is described. The imaging device includes an array of transducers. Each transducer includes an array of piezoelectric elements. Each piezoelectric element transmits pressure waves towards an object to be imaged and receives reflections of the pressure waves off the object to be imaged. The imaging device also includes a transmit channel per one or more piezoelectric elements to generate the pressure waves and a receive channel per one or more piezoelectric elements to process the reflections of the pressure waves. The number of channels are selectively altered to control parameters such as power consumption and temperature.

20 Claims, 32 Drawing Sheets

Related U.S. Application Data

(60) Provisional application No. 62/736,283, filed on Sep. 25, 2018.

(51) Int. Cl.
*A61B 8/06* (2006.01)
*A61B 8/14* (2006.01)
*A61N 7/02* (2006.01)

(52) U.S. Cl.
CPC .............. *A61B 8/06* (2013.01); *A61B 8/145* (2013.01); *A61N 7/02* (2013.01)

(58) Field of Classification Search
CPC ....... A61B 8/08; A61B 8/0883; A61B 8/0891; A61B 8/488; A61B 8/46; A61B 8/4483; A61B 8/4488; A61B 8/546; A61B 8/56; A61N 7/02; A61N 2007/0043; A61N 2007/0078; A61N 2007/0095; A61N 7/022; G01N 29/2437; G01N 29/262; G01N 2291/02475; G01N 29/0654; G01N 29/348; G01N 29/0645
See application file for complete search history.

(56) References Cited

U.S. PATENT DOCUMENTS

| | | | | |
|---|---|---|---|---|
| 4,375,042 A * | 2/1983 | Marcus | H10N 30/857 | 310/330 |
| 4,731,865 A * | 3/1988 | Sievenpiper | G06T 5/40 | 382/128 |
| 5,160,870 A * | 11/1992 | Carson | B06B 1/0629 | 310/334 |
| 5,230,340 A * | 7/1993 | Rhyne | G01S 7/52046 | 600/447 |
| 5,520,187 A * | 5/1996 | Snyder | G01S 7/52034 | 600/447 |
| 5,605,154 A * | 2/1997 | Ries | G01S 15/8934 | 600/463 |
| 5,906,580 A * | 5/1999 | Kline-Schoder | B06B 1/064 | 600/459 |
| 5,957,846 A * | 9/1999 | Chiang | G01S 7/52053 | 600/447 |
| 5,969,621 A * | 10/1999 | Getman | B06B 1/0692 | 310/369 |
| 6,023,977 A * | 2/2000 | Langdon | G01N 29/06 | 600/443 |
| 6,083,168 A * | 7/2000 | Hossack | G01S 7/52085 | 600/443 |
| 6,108,121 A * | 8/2000 | Mansell | G02B 26/0841 | 359/224.1 |
| 6,359,367 B1 * | 3/2002 | Sumanaweera | B06B 1/0292 | 310/309 |
| 6,542,846 B1 * | 4/2003 | Miller | G01S 7/52096 | 702/132 |
| 7,005,776 B1 * | 2/2006 | Iino | H02N 2/145 | 310/323.12 |
| 7,046,734 B2 * | 5/2006 | McVeigh | H04N 19/137 | 375/E7.15 |
| 7,532,093 B1 * | 5/2009 | Pulskamp | H01H 57/00 | 333/262 |
| 8,004,158 B2 * | 8/2011 | Hielscher | B06B 1/0611 | 310/346 |
| 10,835,209 B2 * | 11/2020 | Haque | A61B 8/4488 | |
| 11,058,396 B2 * | 7/2021 | Haque | A61B 8/145 | |
| 11,199,062 B2 * | 12/2021 | Haque | A61B 8/4494 | |
| 11,504,093 B2 * | 11/2022 | Haque | G01S 15/8977 | |
| 11,971,477 B2 * | 4/2024 | Haque | A61B 8/488 | |
| 2001/0005776 A1 * | 6/2001 | Holley | G01S 7/52087 | 600/458 |
| 2003/0178914 A1 * | 9/2003 | Ogawa | H10N 30/045 | 310/311 |
| 2003/0181814 A1 * | 9/2003 | Ji | A61B 8/13 | 600/453 |
| 2004/0190377 A1 * | 9/2004 | Lewandowski | B06B 1/0292 | 367/174 |
| 2004/0195937 A1 * | 10/2004 | Matsubara | H03H 9/02102 | 310/320 |
| 2005/0025377 A1 * | 2/2005 | Avinash | G06T 5/70 | 382/260 |
| 2005/0169107 A1 * | 8/2005 | Thomenius | H03M 11/00 | 367/105 |
| 2005/0228282 A1 * | 10/2005 | Wang | G01S 7/52046 | 600/453 |
| 2005/0228284 A1 * | 10/2005 | Baumgartner | A61B 8/4444 | 600/459 |
| 2006/0113866 A1 * | 6/2006 | Ganor | H02N 2/0075 | 310/323.03 |
| 2006/0122486 A1 * | 6/2006 | Tamez-Pena | A61B 5/055 | 600/410 |
| 2006/0173313 A1 * | 8/2006 | Liu | G01S 15/8993 | 600/437 |
| 2007/0167752 A1 * | 7/2007 | Proulx | G01S 15/8925 | 600/437 |
| 2008/0255451 A1 * | 10/2008 | Cohen | G01S 7/52085 | 600/443 |
| 2009/0069686 A1 * | 3/2009 | Daft | B06B 1/0292 | 310/309 |
| 2010/0020645 A1 * | 1/2010 | Wodnicki | G10K 11/004 | 367/155 |
| 2010/0168576 A1 * | 7/2010 | Poland | G01S 7/5208 | 600/443 |
| 2010/0168583 A1 * | 7/2010 | Dausch | B06B 1/0622 | 600/466 |
| 2010/0266186 A1 * | 10/2010 | Hebrank | G01R 33/56518 | 324/309 |
| 2011/0051461 A1 * | 3/2011 | Buchwald | H02M 3/33507 | 363/15 |
| 2011/0120971 A1 * | 5/2011 | Martin | B81C 1/00904 | 216/41 |
| 2011/0249878 A1 * | 10/2011 | Pagoulatos | G06T 5/50 | 382/131 |
| 2012/0116220 A1 * | 5/2012 | Burcher | A61B 8/00 | 600/438 |
| 2012/0127136 A1 * | 5/2012 | Schneider | G02F 1/13718 | 349/23 |
| 2012/0146642 A1 * | 6/2012 | Du | G01R 33/5619 | 324/309 |
| 2012/0319535 A1 * | 12/2012 | Dausch | H10N 30/2047 | 310/365 |
| 2013/0206962 A1 * | 8/2013 | Barr | H10F 39/199 | 438/59 |
| 2013/0303919 A1 * | 11/2013 | Corl | A61B 8/445 | 600/467 |
| 2014/0024928 A1 * | 1/2014 | Boctor | A61M 25/00 | 600/424 |
| 2014/0117812 A1 * | 5/2014 | Hajati | B06B 1/0276 | 310/314 |
| 2014/0155747 A1 * | 6/2014 | Bennett | H04R 31/00 | 600/439 |
| 2014/0184027 A1 * | 7/2014 | Rice | H10N 30/2048 | 216/17 |
| 2014/0219063 A1 * | 8/2014 | Hajati | B25J 15/12 | 310/334 |
| 2014/0221838 A1 * | 8/2014 | Loupas | G01S 7/52071 | 600/454 |
| 2014/0226430 A1 * | 8/2014 | Bloch | B01F 35/211 | 366/111 |
| 2014/0232241 A1 * | 8/2014 | Hajati | B81B 7/02 | 310/317 |
| 2014/0276069 A1 * | 9/2014 | Amble | A61B 8/4488 | 600/447 |
| 2014/0276087 A1 * | 9/2014 | Corl | B06B 1/0292 | 216/13 |
| 2014/0328504 A1 * | 11/2014 | Stephanou | H10N 30/07 | 381/190 |
| 2014/0355377 A1 * | 12/2014 | Hiriyannaiah | G10K 11/341 | 367/7 |

(56) References Cited

U.S. PATENT DOCUMENTS

| | | | |
|---|---|---|---|
| 2015/0023561 A1* | 1/2015 | Hamilton | A61B 8/06 382/103 |
| 2015/0087988 A1* | 3/2015 | Lee | B06B 1/0622 600/459 |
| 2015/0158052 A1* | 6/2015 | Latev | B06B 1/0622 156/60 |
| 2015/0160322 A1* | 6/2015 | Matthews | G01R 33/56341 324/322 |
| 2015/0265245 A1* | 9/2015 | von Ramm | B06B 1/0625 600/443 |
| 2015/0272547 A1* | 10/2015 | Freiburger | A61B 8/52 600/438 |
| 2015/0333730 A1* | 11/2015 | Meltaus | H03H 9/175 310/321 |
| 2016/0107194 A1* | 4/2016 | Panchawagh | B06B 1/0644 310/317 |
| 2016/0211828 A1* | 7/2016 | Simmonds | G02B 6/1225 |
| 2016/0262725 A1* | 9/2016 | Boser | A61B 8/4483 |
| 2016/0288168 A1* | 10/2016 | Hynynen | A61N 7/02 |
| 2016/0331345 A1* | 11/2016 | Kong | A61B 8/5207 |
| 2017/0000461 A1* | 1/2017 | Wong | G06T 7/0012 |
| 2017/0224312 A1* | 8/2017 | Call | G01S 15/8952 |
| 2017/0262598 A1* | 9/2017 | Petkov | G06N 3/045 |
| 2017/0328870 A1* | 11/2017 | Garlepp | G11C 19/38 |
| 2018/0116632 A1* | 5/2018 | Yoo | G01N 29/2437 |
| 2018/0153510 A1* | 6/2018 | Haque | B06B 1/0238 |
| 2018/0153512 A1* | 6/2018 | Akkaraju | H10N 30/88 |
| 2018/0154393 A1* | 6/2018 | Viegas | B06B 1/0238 |
| 2018/0154394 A1* | 6/2018 | Haque | A61B 8/4488 |
| 2018/0192999 A1* | 7/2018 | Song | A61B 8/4405 |
| 2019/0184426 A1* | 6/2019 | Kojima | H10N 30/802 |
| 2019/0290243 A1* | 9/2019 | Bryzek | H01L 24/73 |
| 2019/0316957 A1* | 10/2019 | Akkaraju | H10N 30/852 |
| 2019/0316958 A1* | 10/2019 | Akkaraju | G01N 29/0654 |
| 2020/0046320 A1* | 2/2020 | Wodnicki | B06B 1/0622 |
| 2020/0225082 A1* | 7/2020 | Akkaraju | H01G 5/00 |
| 2020/0249079 A1* | 8/2020 | Akkaraju | G01N 29/07 |
| 2021/0022706 A1* | 1/2021 | Haque | G01S 7/52046 |
| 2021/0022707 A1* | 1/2021 | Haque | H10N 30/2048 |
| 2021/0124044 A1* | 4/2021 | Haque | A61B 8/08 |
| 2021/0137497 A1* | 5/2021 | Bryzek | B81C 1/00238 |
| 2021/0172788 A1* | 6/2021 | Akkaraju | G01S 7/5208 |
| 2021/0275143 A1* | 9/2021 | Haque | A61B 8/4494 |
| 2021/0278530 A1* | 9/2021 | Haque | G01S 15/8913 |
| 2021/0293952 A1* | 9/2021 | Haque | G01S 15/8925 |
| 2023/0200781 A1* | 6/2023 | Haque | A61B 8/5207 |
| 2024/0280696 A1* | 8/2024 | Haque | G01N 29/0654 |

FOREIGN PATENT DOCUMENTS

| | | | | |
|---|---|---|---|---|
| CA | 3105459 C | * | 8/2023 | ........... A61B 5/0095 |
| WO | WO-2020068473 A1 | * | 4/2020 | ........... A61B 5/0095 |
| WO | WO-2022198045 A1 | * | 9/2022 | ........... G01S 15/892 |

* cited by examiner

IMAGING DEVICES WITH SELECTIVELY ALTERABLE CHARACTERISTICS

CROSS REFERENCE TO RELATED APPLICATIONS

This application is a Divisional of U.S. patent application Ser. No. 17/257,175, filed on Dec. 30, 2020, which is a National Stage Entry of International Application No. PCT/US2019/051328, filed on Sep. 16, 2019, which claims the benefit of and priority to U.S. Provisional Application No. 62/736,283, filed on Sep. 25, 2018, the entireties of each of which are incorporated herein by reference.

BACKGROUND

The present invention relates to imaging devices, and more particularly to imaging devices having electronically configurable ultrasonic imagers. Non-intrusive imaging devices can be used to image internal tissue, bones, blood flow, or organs of human or animal bodies. The images can then be displayed. To perform the imaging, the imaging devices transmit a signal into the body and receive a reflected signal from the body part being imaged. Such imaging devices include transducers and associated electronics, which may be referred to as transceivers or imagers, and which may be based on photo-acoustic or ultrasonic effects. Such transducers can be used for imaging and can be used in other applications as well. For example, the transducers can be used in medical imaging; flow measurements in pipes, speaker, and microphone arrays; lithotripsy; localized tissue heating for therapeutic; and highly intensive focused ultrasound (HIFU) surgery.

BRIEF DESCRIPTION OF THE DRAWINGS

The accompanying drawings illustrate various examples of the principles described herein and are part of the specification. The illustrated examples are given merely for illustration, and do not limit the scope of the claims.

Figure 1:
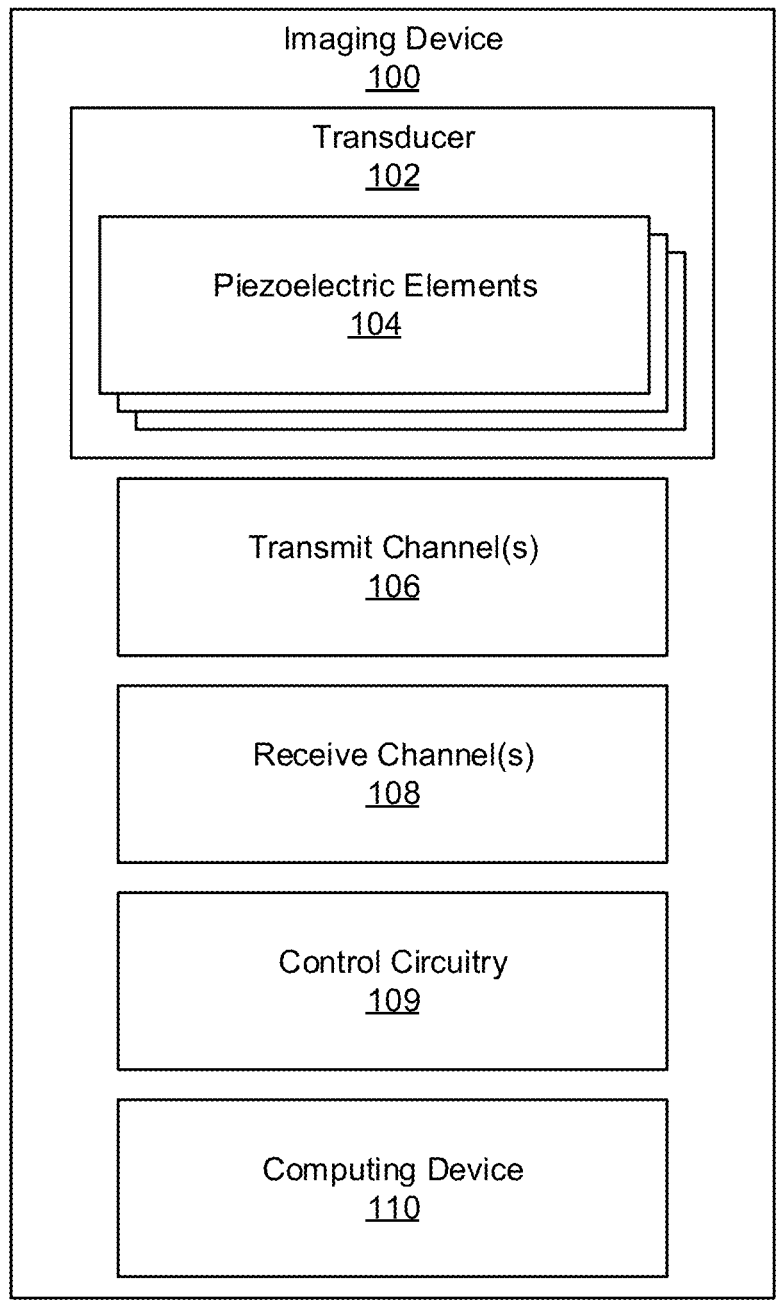
FIG. 1 is a block diagram of an imaging device with selectively alterable characteristics, according to an example of the principles described herein.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION

As described above, the present invention relates to imaging devices, and more particularly to imaging devices having electronically configurable ultrasonic imagers. Non-intrusive imaging devices can be used to image internal tissue, bones, blood flow, or organs of human or animal bodies. The images can then be displayed. To perform the imaging, the imaging devices transmit a signal into the body and receive a reflected signal from the body part being imaged. Such imaging devices include transducers, which may be referred to as transceivers or imagers, and which may be based on photo-acoustic or ultrasonic effects. Such transducers can be used for imaging and can be used in other applications as well. For example, the transducers can be used in medical imaging; flow measurements in pipes, speaker, and microphone arrays; lithotripsy; localized tissue heating for therapeutic; and highly intensive focused ultrasound (HIFU) surgery.

Imaging devices such as ultrasound imagers used in medical imaging use piezoelectric (PZT) material or other piezo ceramic and polymer composites. Such imaging devices house the transducers with the PZT material as well as other electronics that form and display the image on a display unit. To fabricate the bulk PZT elements for the transducers, a thick piezoelectric material slab can be cut into large rectangular shaped PZT elements. These rectangular-shaped PZT elements are very expensive to build, since the manufacturing process involves precisely cutting of the rectangular-shaped thick PZT or ceramic material and mounting it on substrates with precise spacing. Further, the impedance of the transducers is much higher than the impedance of the transmit/receive electronics for the transducers, which can affect performance.

Still further, such thick bulk PZT elements can require very high voltage pulses, for example 100 volts (V) or more to generate transmission signals. This high drive voltage results in high power dissipation, since the power dissipation in the transducers is proportional to the square of the drive voltage. This high-power dissipation generate heat within the imaging device such that cooling arrangements are necessitated. These cooling systems increase the manufacturing costs and weights of the imaging devices which makes the imaging devices more burdensome to operate.

Even further, the transmit/receive electronics for the transducers may be located far away from the transducers themselves, thus requiring micro-coax cables between the transducers and transmit/receive electronics. In general, the cables have a precise length for delay and impedance matching, and, quite often, additional impedance matching networks are used for efficient connection of the transducers through the cables to the electronics.

Accordingly, the present specification describes the use of piezoelectric micromachined ultrasound transducers (pMUTs), which can be efficiently formed on a substrate leveraging various semiconductor wafer manufacturing operations. Semiconductor wafers may come in 6 inch, 8 inch, and 12 inch sizes and are capable of housing hundreds of transducer arrays. These semiconductor wafers start as a silicon substrate on which various processing steps are performed. An example of such an operation is the formation of SiO2 layers, also known as insulating oxides. Various other steps such as the addition of metal layers to serve as interconnects and bond pads are performed to allow connection to other electronics. Yet another example of a machine operation is the etching of cavities. Compared to the conventional transducers having bulky piezoelectric material, pMUTs built on semiconductor substrates are less bulky, are cheaper to manufacture, and have simpler and higher performance interconnection between electronics and transducers. As such, they provide greater flexibility in the operational frequency, and potential to generate higher quality images.

In some examples the imaging device is coupled to an application specific integrated circuit (ASIC) that includes transmit drivers, sensing circuitry for received echo signals, and control circuitry to control various operation. The ASIC can be formed on another semiconductor wafer. This ASIC can be placed in close proximity to pMUT elements to reduce parasitic losses. As a specific example, the ASIC may be 50 micrometers (um) or less away from the transducer array. In a broader example, there may be less than 100 um separation between the 2 wafers or 2 die, where each wafer includes many die and a die includes a transducer in the transducer wafer and an ASIC in the ASIC wafer. In some examples, ASIC has matching dimensions relative to the pMUT and allows the devices to be stacked for wafer-to-wafer interconnection or transducer die on ASIC wafer or transducer die to ASIC die interconnection. Alternatively, the transducer can also be developed on top of the ASIC wafer using low temperature piezo material sputtering and other low temperature processing compatible with ASIC processing.

While pMUTs have potential for advanced ultrasonic imaging, some limitations have impeded their utilization in high performance imaging implementation. As an example, pMUTs utilizing Aluminum Nitride have exhibited low sensitivity related to transmit and receive operations making them candidates for less demanding applications. Other pMUTs utilizing PZT have required relatively high voltages and exhibit relatively low bandwidth and low efficiency. Accordingly, the present specification describes pMUTs that 1) have an enhanced sensitivity, 2) can operate at low voltages, and 3) exhibit high bandwidth linear operation. Specifically, the present specification describes pMUTs in close proximity to the associated control circuitry. This allows 2D and 3D imaging under control of a control circuitry in a small portable device. Another type of transducer is a capacitive micromachine ultrasonic transducer (cMUT). However, cMUT sensors have difficulty with generating sufficient acoustic pressure at lower frequencies (where the bulk of deep medical imaging occurs) are inherently nonlinear, cMUTs require high voltage operation.

In general, an imaging device of the present specification includes a number of transmit channels and a number of receive channels. Transmit channels drive the piezoelectric elements with a voltage pulse at a frequency the elements are responsive to. This causes an ultrasonic waveform to be emitted from the piezoelectric elements which waveform is directed towards an object to be imaged. In some examples, the imaging device with the transducer array of piezoelectric elements makes mechanical contact with the body using a gel in between the imaging device and the body. The ultrasonic waveform travels towards the object, i.e., an organ, and a portion of the waveform is reflected back to the piezoelectric elements, where the received ultrasonic energy is converted to an electrical energy, which is then further processed by a number of receive channels and other circuitry to develop an image of the object.

These transmit and receive channels consume power and in instruments where there are many channels (to generate high quality images), the power may cause excessive heat buildup in the imaging device. If the temperature rises past a certain value, it may affect operation of the imaging device, could pose a danger to the operator, could pose a danger to a patient, and may be outside of regulatory specifications which restrict how high the temperature can rise. An ultrasound imaging device includes a transducer array, an application-specific integrated circuit (ASIC), transmit and receive beamforming circuitry, and control electronics. Specifications restrict the maximum temperature that can be tolerated, which in turn, severely restricts what electronic circuits can he housed in the imaging device and also restricts how the imaging device is operated. Such restrictions can negatively affect the image quality achieved and the frame rate of images. Further, imaging devices may be battery-powered which may drain quickly in instruments with many channels as each channel draws energy.

The imaging device of the present specification resolves these and other issues. Specifically, the imaging device controls power dissipation without exceeding temperature limits of the imaging device all while maintaining needed image quality. Specifically, the number of receive channels and/or transmit channels used to form an image are electronically adaptable to save power, for example in cases where a lower number of channels is acceptable. As a specific example, each of the number of channels may be dynamically controlled to reduce power, or to be powered down entirely. Additionally, other characteristics of each channel are also configurable to reduce power. Such advanced control allows the imaging device to be operated within safe temperature thresholds, and may do so without sacrificing needed image quality. The lower power consumption also increases battery life.

Specifically, the imaging device includes a handheld casing where transducers and associated electronics are housed. The imaging device may also contain a battery to power the electronics. As described above, the amount of power consumed by the imaging device increases the temperature of the imaging device. To ensure satisfactory use of the imaging device and imaging device performance, the temperature of the body of the imaging device should remain below a threshold temperature. The imaging device of the present specification is electronically configured to reduce power and temperature notwithstanding the acquisition of high-quality images which consumes significant amount of power, reduces battery life, and increases temperature in the probe.

That is, the present specification describes a high performance, low power, and low-cost portable imaging device capable of 2D and 3D imaging using pMUTs in a 2D array built on a silicon wafer. Such an array coupled to an application specific integrated circuit (ASIC) with electronic configuration of certain parameters, enables a higher quality of image processing at a low cost than has been previously possible. Further by controlling certain parameters, for example the number of channels used, power consumption can be altered and temperature can be changed.

In summary, the present specification describes an imaging device that relies on pMUT-based transducers connected to control electronics on a per pixel basis and housed in a portable housing. The imaging device allows system configurability and adaptability in real time to actively control power consumption and temperature in the imaging device. This is done by minimizing power dissipation within the imaging device by 1) altering the number of channels and/or 2) actively controlling power dissipation in those channels such that temperatures within the imaging device do not exceed specification limits. All this is done while achieving superior performance than would otherwise be possible.

In the following description, for purposes of explanation, specific details are set forth in order to provide an understanding of the disclosure. It will be apparent, however, to one skilled in the art that the disclosure can be practiced without these details. Furthermore, one skilled in the art will recognize that examples of the present disclosure, described below, may be implemented in a variety of ways, such as a process, an apparatus, a system, a device, or a method on a tangible computer-readable medium.

One skilled in the art shall recognize: (1) that certain fabrication steps may optionally be performed; (2) that steps may not be limited to the specific order set forth herein; and (3) that certain steps may be performed in different orders, including being done contemporaneously.

Elements/components shown in diagrams are illustrative of exemplary embodiments of the disclosure and are meant to avoid obscuring the disclosure. Reference in the specification to "one example," "preferred example," "an example," or "examples" means that a particular feature, structure, characteristic, or function described in connection with the example is included in at least one example of the disclosure and may be in more than one example. The appearances of the phrases "in one example," "in an example," or "in examples" in various places in the specification are not necessarily all referring to the same example or examples. The terms "include," "including," "comprise," and "comprising" shall be understood to be open terms and any lists that follow are examples and not meant to be limited to the listed items. Any headings used herein are for organizational purposes only and shall not be used to limit the scope of the description or the claims. Furthermore, the use of certain terms in various places in the specification is for illustration and should not be construed as limiting.

In some examples, the manufacturing cost of pMUTs described herein may be reduced by applying modern semiconductor and wafer processing techniques. For example, a thin film piezoelectric layer may be spun on or sputtered onto semiconductor wafers and later patterned to create piezoelectric sensors that each have two or more electrodes. In one example, each piezoelectric element may be designed to have the ability to emit or receive signals at a certain frequency, known as center frequency, as well as the second and/or additional frequencies.

As used in the present specification and in the appended claims, the term piezoelectric element, pMUT, transceiver, and pixel are used interchangeably.

Turning now to the figures, FIG. 1 is a block diagram of an imaging device (100) with selectively alterable channels (106, 108), controlled by a controller (109), and having imaging computations performed on a computing device (110) according to principles described herein. As described above, the imaging device (100) may be used to generate an image of internal tissue, bones, blood flow, or organs of human or animal bodies. Accordingly, the imaging device (100) transmits a signal into the body and receives a reflected signal from the body part being imaged. Such imaging devices include piezoelectric transducers, which may be referred to as transceivers or imagers, which may be based on photo-acoustic or ultrasonic effects. The imaging device (100) can be used to image other objects as well. For example, the imaging device can be used in medical imaging; flow measurements in pipes, speaker, and microphone arrays; lithotripsy; localized tissue heating for therapeutic; and highly intensive focused ultrasound (HIFU) surgery.

In addition to use with human patients, the imaging device (100) may be used to get an image of internal organs of an animal as well. Moreover, in addition to imaging internal organs, the imaging device (100) may also be used to determine direction and velocity of blood flow in arteries and veins as in Doppler mode imaging and may also be used to measure tissue stiffness.

The imaging device (100) may be used to perform different types of imaging. For example, the imaging device (100) may be used to perform one dimensional imaging, also known as A-Scan, two-dimensional imaging, also known as B scan, three dimensional imaging, also known as C scan, and Doppler imaging. The imaging device (100) may be switched to different imaging modes and electronically configured under program control.

To facilitate such imaging, the imaging device (100) includes an array of piezoelectric transducers (102), each piezoelectric transducer (102) including an array of piezoelectric elements (104). The piezoelectric elements (104) operate to 1) generate the pressure waves that are passed through the body or other mass and 2) receive reflected waves off the object within the body, or other mass, to be imaged. In some examples, the imaging device (100) may be configured to simultaneously transmit and receive ultrasonic waveforms. For example, certain piezoelectric elements (104) may send pressure waves toward the target object being imaged while other piezoelectric elements (104) receive the pressure waves reflected from the target object and develop electrical charges in response to the received waves.

In some examples, each piezoelectric element (104) may be designed to have the ability to emit or receive signals at a certain frequency, known as a center frequency, as well as the second and/or additional frequencies. Such multi-frequency piezoelectric elements (104) may be referred to as multi-modal piezoelectric elements (104) and can expand the bandwidth of the imaging device (100).

The piezoelectric material that forms the piezoelectric elements (104) contracts and expands when different voltage values at a certain frequency are applied. Accordingly, as voltages that alternates between different values are applied, the piezoelectric elements (104) transform the electrical energy (i.e., voltages) into mechanical movements resulting in acoustic energy which is emitted as waves at the desired frequencies. These waves are reflected from a target being imaged and are received at the same piezoelectric elements (104) and converted into electrical signals that are then used to form an image of the target.

To generate the pressure waves, the imaging device (100) includes a number of transmit channels (106) and a number of receive channels (108). The transmit channels (106) include a number of components and drive the transducer (102), i.e., the array of piezoelectric elements (104), with a voltage pulse at a frequency that they are responsive to. This causes an ultrasonic waveform to be emitted from the piezoelectric elements (104) towards an object to be imaged. The ultrasonic waveform travels towards the object to be imaged and a portion of the waveform is reflected back to the transducer (102), where the receive channels (108) collect the reflected waveform, convert it to an electrical energy, and process it, for example at the computing device (110), to develop an image that can be displayed.

In some examples, while the number of transmit channels (106) and receive channels (108) in the imaging device (100) may remain constant, the number of piezoelectric elements (104) that they are coupled to may vary. This coupling is controlled by the controller (109). In some examples, a portion of the control circuitry may be distributed in the transmit channels (106) and in the receive channels (108). For example, the piezoelectric elements (104) of a transducer (102) may be formed into a two-dimensional array with N columns and M rows. In a specific example, the two-dimensional array of piezoelectric elements (104) may have 128 columns and 32 rows. In this example, the imaging device (100) may have up to 128 transmit channels (106) and up to 128 receive channels (108). In this example, each transmit channel (106) and receive channel (108) may be coupled to multiple or single piezoelectric elements (104). For example, depending on the imaging mode, each column of piezoelectric elements (104) may be coupled to a single transmit channel (106) and a single receive channel (108). In this example, the transmit channel (106) and receive channel (108) may receive composite signals, which composite signals combine signals received at each piezoelectric element (104) within the respective column. In another example, i.e., during a different imaging mode, individual piezoelectric elements (104) may be coupled to their own transmit channel (106) and their own receive channel (108).

These transmit and receive channels (106, 108) consume power. In high end instruments where there are many channels for generating high quality images, the power may cause excessive heat buildup in the imaging device (100). Excess heat can be uncomfortable, and in some cases pose a danger to a patient on whom the imaging device (100) is placed for imaging Such excess heat is also problematic for an operator of the imaging device (100). Still further, the excess heat may damage the components of the imaging device (100) rendering the imaging device (100) ineffective, or perhaps even inoperable. Accordingly, the transmit channels (106) and receive channels (108) are selectively adaptable to 1) reduce power consumption, 2) prevent excess heat buildup, and 3) optimize imaging performance and power consumption needs in real time, i.e. dynamically.

Selectively adjusting the channels (106, 108) may include placing the channels (106, 108) in a powered down state, or placing them in a lower power state. Adjusting the channels (106, 108) may be on a per-channel basis. For example, all or some of the receive channels (108) may be powered down or placed in a low power state and some or all of the transmit channels (106) may be powered down or placed in a low power state. Specific examples of altering the number of channels (106, 108) are provided in the description that follows. Allowing for the adjustment of channels (106, 108) prevents excess heat buildup by turning off power consuming (and heat generating) components at times when a threshold heat is exhibited by the imaging device (100).

For example, when power consumption is to be reduced, an imaging session could be designed such that instead of high resolution, the session includes low resolution imaging when high resolution is not needed and includes high resolution imaging when desired. Such a system can be dynamically controlled using fast configurable transmit and receive circuitry to achieve lower power, where lower resolution can use smaller number of channels or channels that operate at lower power but with higher noise (which results in lower resolution)

Figure 2:
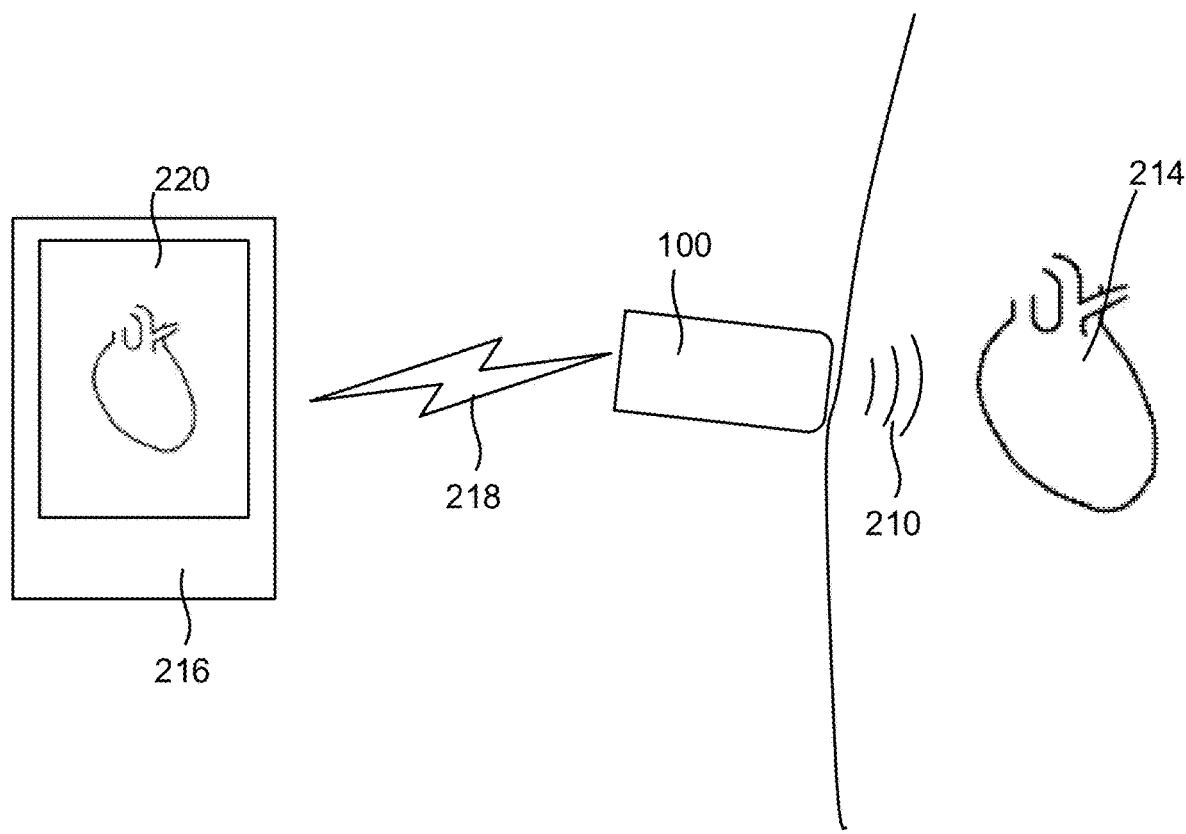
FIG. 2 is a diagram of an imaging system with selectively alterable characteristics, according to an example of the principles described herein.

FIG. 2 is a diagram of an imaging system with selectively configurable characteristics, according to an example of the principles described herein. As depicted, the imaging system includes the imaging device (100) that generates and transmits, via the transmit channels (FIG. 1, 106) pressure waves (210) toward an internal organ, such as a heart (214), in a transmit mode/process. The internal organ, or other object to be imaged, may reflect a portion of the pressure waves (210) toward the imaging device (100) which captures, via the transducer (FIG. 1,102), receive channels (FIG. 1, 108), control circuitry (FIG. 1, 109), and computing device (FIG. 1,110), the reflected pressure waves and generates electrical signals in a receive mode/process. The system also includes another computing device (216) that communicates with the imaging device (100) through a communication channel (218). The imaging device (100) may communicate electrical signals to the computing device (216) which processes the received signals to complete formation of an image of the object. A display device (220) of the system can then display images of the organ or target using the electrical signals.

Figure 3:
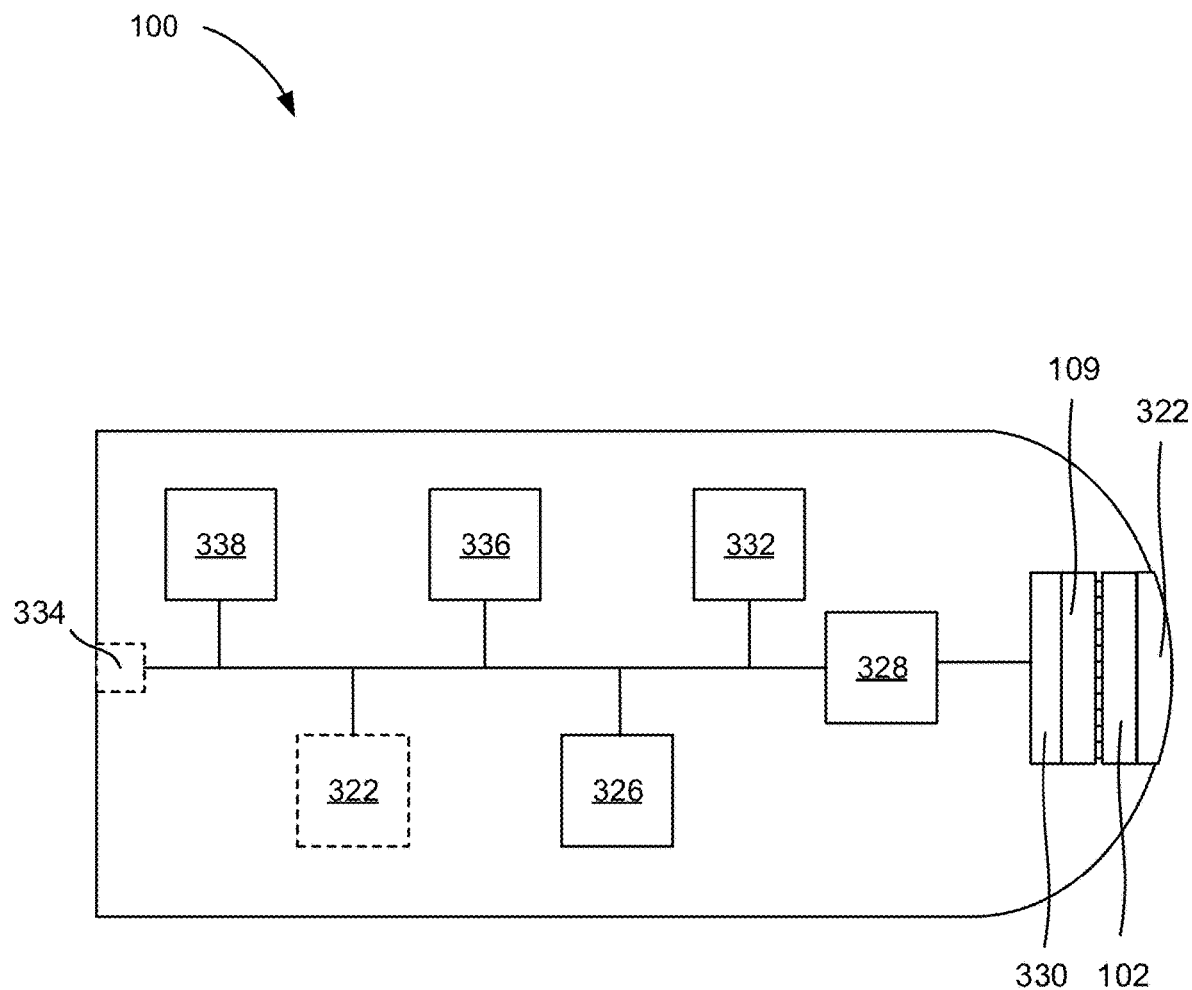
FIG. 3 is a schematic diagram of an imaging device with selectively alterable characteristics, according to an example of the principles described herein.

As depicted in FIG. 2, the imaging device (100) may be a portable, handheld device that communicates signals through the communication channel (218), either wirelessly (using a protocol, such as 802.11 protocol) or via a cable (such as USB2, USB 3, USB 3.1, and USB-C), with the computing device (216). In the case of a tethered connection, the imaging device (100) may include a port as depicted in FIG. 3 for receiving the cable that is to communicate with the computing device (216). In the case of a wireless connect, the imaging device (100) includes a wireless transmitter to communicate with the computing device (216).

As depicted in FIG. 2, the display device (220) and the computing device (216) may be separate from the imaging device (100). For example, the computing device (216) and display device (220) may be disposed within a separate device, i.e., a mobile device, such as cell phone or iPad, or a stationary computing device, which can display images to a user. In another example, the display device (220) and the computing device (220) are contained within the imaging device (100). That is, the imaging device (100), computing device (216), and display device (220) may be disposed within a single housing.

FIG. 3 is a schematic diagram of an imaging device (100) with selectively alterable characteristics, according to an example of the principles described herein. As described above, the imaging device (100) may be an ultrasonic medical probe. FIG. 3 depicts the transducer(s) (102) of the imaging device (100). As described above, the transducer(s) (102) include arrays of piezoelectric elements (FIG. 1, 104) that transmit and receive pressure waves (FIG. 2, 210). In some examples, the imaging device (100) includes a coating layer (322) that serves as an impedance matching interface between the transducers (102) and the human body, or other mass through which the pressure waves (FIG. 2, 210) are transmitted. In some cases, the coating layer (322) may serve as a lens when designed with the curvature consistent with focal length desired.

In embodiments, the user may apply gel on the skin of the human body before a direct contact with the coating layer (322) so that the impedance matching at the interface between the coating layer (322) and the human body may be improved. Impedance matching reduces the loss of the pressure waves (FIG. 2, 210) at the interface and the loss of the reflected wave travelling toward the imaging device (100) at the interface.

In some examples, the coating layer (322) may be a flat layer to maximize transmission of acoustic signals from the transducer(s) (102) to the body and vice versa. The thickness of the coating layer (322) may be a quarter wavelength of the pressure wave (FIG. 2, 210) generated by the transducer(s) (102).

The imaging device also includes a controller (109), such as an application-specific integrated circuit (ASIC chip or ASIC), for controlling the transducers (102). The controller (109) is coupled to the transducers (102) by bumps. As described above, the transmit channels (106) and receive channels (108) may be selectively alterable meaning that the quantity of transmit channels (106) and receive channels (108) that are active at a given time may be altered such that the power consumption characteristics of the transmit channels (106) and receive channels (108) may be altered. For example, it may be the case that the channels that are selectively altered are receive channels (FIG. 1, 108) that are powered down or set to a lower power state. The receive channels (FIG. 1, 108) include various components to receive the reflected pressure waves (FIG. 2, 210) and convert them to electrical signals. These components consume power and accordingly, by powering down the receive channel (FIG. 1, 108) or setting it to a lower power mode, these components draw less power and thus decrease their heat generation. Specific details regarding the receive channel (FIG. 1, 108) and the components that can be powered down or set to a low powered mode are described later in the specification.

In another example, it may be that the transmit channels (FIG. 1, 106) are powered down or set to a lower power state. With specific regards to the transmit channels (FIG. 1, 108), the transmit channels (FIG. 1, 108) drive the piezoelectric elements (FIG. 1, 104) via a voltage pulse of a predetermined value, for example 15 volts (V). In some examples, placing the transmit channels (FIG. 1, 106) in a lower power state may mean reducing the magnitude of the voltage pulse, for example to 5 V.

In some examples, the basis for altering the channels may be a mode of operation. For example, the imaging device (100) may operate in a low-resolution mode that results in lower resolution images and/or a higher resolution mode that results in higher resolution images. The resolution of an image may refer to the number of scan lines for a particular frame of an image or the number of frames generated per second. Accordingly, generating a higher resolution image may require the use of more channels. For example, a high-resolution image may require all 128 receive channels (FIG. 1, 108) and all 128 transmit channels (FIG. 1, 106). However, a lower resolution image may be generated by activating just a subset of the receive channels (FIG. 1, 108) and the transmit channels (FIG. 1, 106), say 64 of each. In some examples, the low power mode may refer to a mode wherein the imaging device (100) is searching for the particular object to be imaged and the high-power mode may refer to a mode wherein the object has been found and high-resolution images of the object are desired. In this example, the number of channels (FIG. 1, 106, 108) are powered down or set to the low power state during the low-resolution portion.

The imaging device (100) may also include Field Programmable Gate Arrays (FPGAs) (326) for controlling the components of the imaging device (100); circuit(s) (328), such as Analog Front End (AFE), for processing/conditioning signals and an acoustic absorber layer (330) for absorbing waves that are generated by the transducers (102) and propagated towards the circuits (328). That is, the transducer(s) (102) may be mounted on a substrate and may be attached to an acoustic absorber layer (330). This layer absorbs any ultrasonic signals that are emitted in the reverse direction, which may otherwise be reflected and interfere with the quality of the image. While FIG. 3 depicts the acoustic absorber layer (330), this component may be omitted in cases where other components prevent a material transmission of ultrasound in the backwards direction, i.e., away from the transducers (102).

The imaging device (100) may include a communication unit (332) for communicating data with an external device, such as the computing device (FIG. 2, 216), through for example a port (334) or a wireless transmitter. The imaging device (100) may include memory (336) for storing data. In some examples, the imaging device (100) includes a battery (338) for providing electrical power to the components of the imaging device (100). The selectable alteration of the channels may have a particularly relevant impact when the imaging device (100) includes a battery (338). For example, as the receive channels (FIG. 1, 108) and transmit channels (FIG. 1, 106) include components that draw power, the battery depletes over time. The consumption of power by these components in some examples may be rather large such that the battery (338) would drain in a short amount of time. This is particularly relevant when obtaining high quality images which consume significant amounts of power. The battery (338) may also include battery charging circuits which may be wireless or wired charging circuits. The imaging device (100) may include a gauge that indicates a battery charge consumed and is used to configure the imaging device (100) to optimize power management for improved battery life.

Accordingly, by reducing the power consumption, or in some cases powering down completely the different channels (FIG. 1, 106, 108), the battery (338) life is extended which enhances the ease of use of the imaging device (100).

Figure 4:
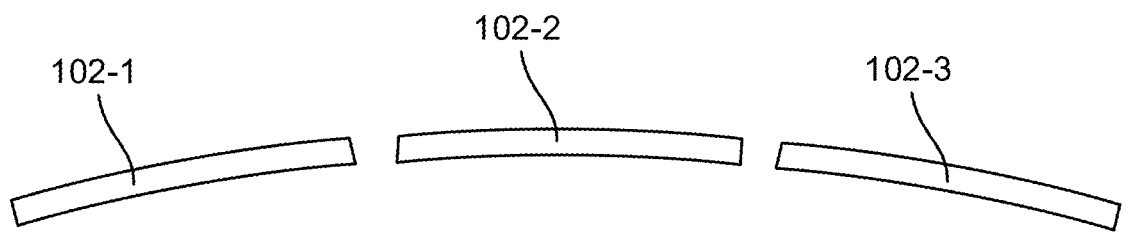
FIG. 4 is a side view of a curved transducer array, according to an example of the principles described herein.
Figure 5:
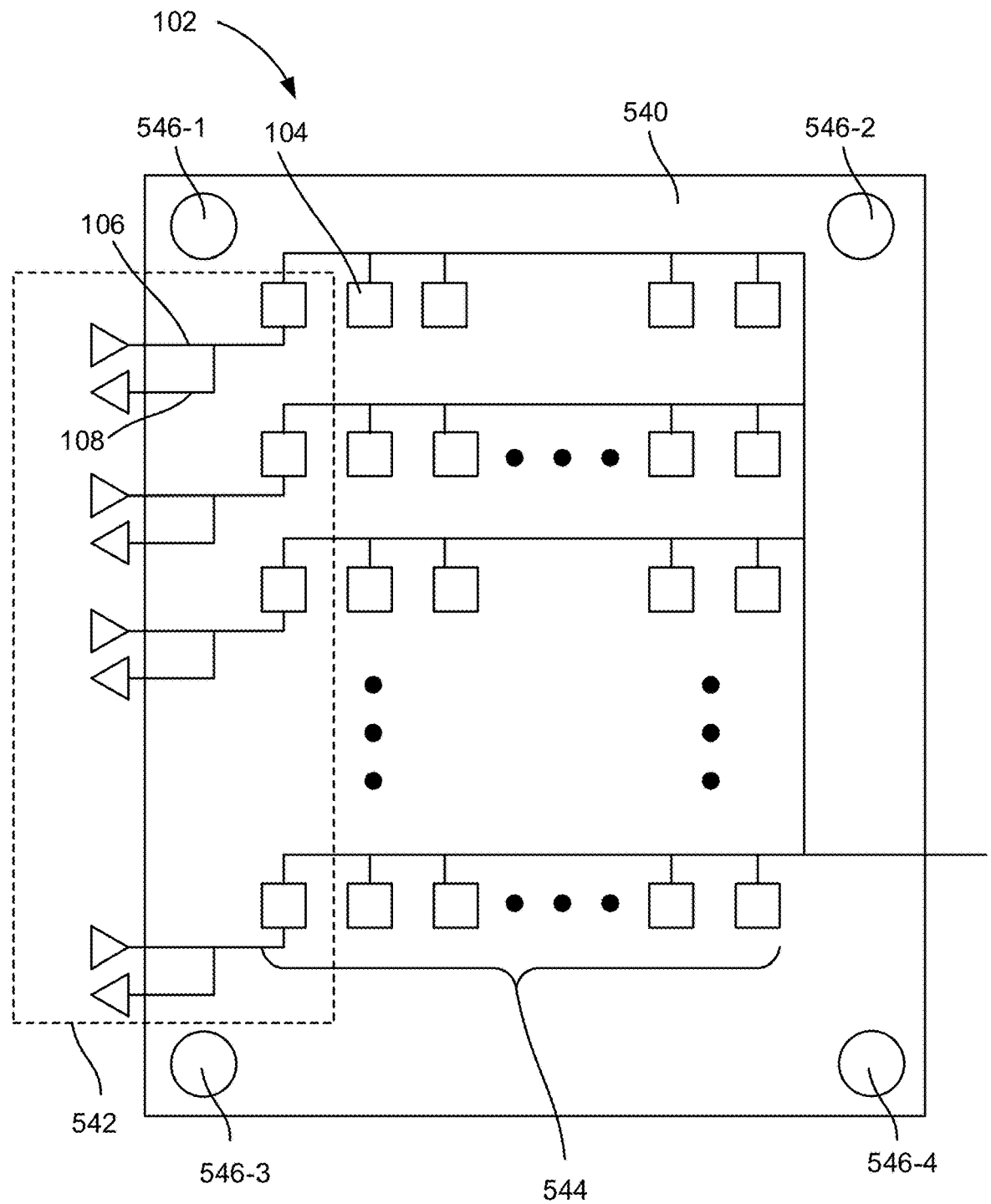
FIG. 5 is a top view of a transducer, according to an example of the principles described herein.

FIG. 4 is a side view of a transducer (102) array, according to an example of the principles described herein. As described above, the imaging device (FIG. 1, 100) may include an array of transducers (102-1, 102-2, 102-3), each with their own array of piezoelectric elements (FIG. 1, 104). In some examples, the transducers (102) may be curved so as to provide a wider angle of the object (FIG. 2, 214) to be imaged. FIG. 5 depicts a top view of a single transducer (102). As depicted in FIG. 5, the transducer (102) may include a transceiver substrate (540) and one or more piezoelectric elements (104) arranged thereon. Unlike the conventional systems that use bulk piezoelectric elements, the piezoelectric element (104) may be formed on a wafer and the wafer may be diced to form multiple transducers (102). This process may reduce the manufacturing cost since the transducers (102) may be fabricated in high volume and at low cost In some examples, the diameter of the wafer may range between 6~12 inches and many piezoelectric element (104) arrays may be batch manufactured thereon. Furthermore, in some examples, the controller (FIG. 1, 109) for controlling the piezoelectric elements (104) may be formed such that each piezoelectric element (104) is connected to the matching integrated circuits, i.e., receive channels (FIG. 1, 108) and transmit channels (FIG. 1, 106) in close proximity, preferably within 25 µm-100 µm. For example, the transducer (102) may have 1,024 piezoelectric elements (104) and be connected to a matching controller (FIG. 1, 109) that has the appropriate number of transmit and receive circuits for the 1,024 piezoelectric elements (104).

Each piezoelectric element (104) may have any suitable shape such as, square, rectangle, and circle. As depicted in FIG. 5, in some examples, the piezoelectric elements (104) may be arranged in a two-dimensional array arranged in orthogonal directions. That is, the piezoelectric element (104) array may be an M×N array with N columns (542) and M rows (544).

To create a line element, a column (542) of N piezoelectric elements (104) may be connected electrically in parallel. Then, this line element may provide transmission and reception of ultrasonic signals similar to those achieved by a continuous piezoelectric element that is almost N times longer than each piezoelectric element (104). This line element may be called a column or line or line element interchangeably. An example of a column of piezo element is shown in FIG. 5 by the reference number (542). Piezoelectric elements (104) are arranged in a column (542) in this example and have associated transmit driver circuits (part of transmit channel) and low noise amplifiers which are part of the receive channel circuitry. Although not explicitly shown, the transmit and receive circuitry include multiplexing and address control circuitry to enable specific elements and sets of elements to be used. It is understood that transducers (102) may be arranged in other shape such as circular, or other shapes. In some examples, each piezoelectric elements (104) may be spaced 250 µm from each other center to center.

In the transducer (102) of the present specification, it is advantageous to design a line element using a plurality of identical piezoelectric elements (104), where each element may have its characteristic center frequency. When a plurality of the piezoelectric elements (104) are connected together, the composite structure (i.e. the line element) may act as one line element with a center frequency that consists of the center frequencies of all the element pixels. In modern semiconductor processes, these center frequencies match well to each other and have a very small deviation from the center frequency of the line element. It is also possible to mix several pixels of somewhat different center frequencies to create a wide bandwidth line compared to lines using only one central frequency.

In some examples, the transducers (102) may include one or more temperature sensors (546-1, 546-2, 546-3, 546-4) to measure the temperature of the transducer (102). While FIG. 5 depicts temperature sensors (546) disposed at particular locations, the temperature sensors (546) may be disposed at other locations on the transducer (102) and additional sensors may be disposed at other locations on the imaging device (FIG. 1, 100).

The temperature sensors (546) may be a trigger to the selective adjustment of channels (FIG. 1, 106, 108). That is, as described above, temperatures within a handheld portable imaging device (FIG. 1, 100) may rise above a predetermined temperature. Accordingly, the temperature sensors (546) may detect a temperature of the device at the transducer (102) surface, which is a surface that contacts a patient. If the temperature sensors (546) detect a temperature greater than a threshold amount, for example a user-established temperature or a temperature set by a regulatory authority, a signal may be passed by the controller (FIG. 3, 324) to power down all or some of the transmit channels (FIG. 1, 106) and/or receive channels (FIG. 1, 108) or to set all or some of the transmit channels (FIG. 1, 106) and/or receive channels (FIG. 1, 108) in a low power state. Placing the temperature sensor (546) on the transducers (102) is beneficial in that this is the surface that contacts the patient and is therefore provides data regarding the temperature at the interface where a user may notice or be affected by excess heat.

FIG. 5 also depicts the terminals of the piezoelectric elements (104). That is, each piezoelectric element (104) has two terminals. A first terminal is a common terminal shared by all piezoelectric elements (104) in the array. The second terminal connects the piezoelectric elements (104) to the transmit channels (FIG. 1, 106) and receive channels (FIG. 1, 108). This second terminal is the terminal that is driven and sensed for every piezoelectric element (104) as shown symbolically for those piezoelectric elements (104) in the first column. For simplicity, the second terminal is only indicated for those piezoelectric elements (104) in the first column. However, similar terminals with the associated transmit channels (106) and receive channels (108) populate the other piezoelectric elements (104) in the array. The controller (FIG. 1, 109) using control signals can select a column (542) of piezoelectric elements (104) by turning on respective transmit channels (FIG. 1, 106) and receive channels (FIG. 1, 108) and turning off the channels (FIG. 1, 106, 108) in other columns (542). In a similar manner, it is also possible to turn off particular rows (54), or even individual, piezoelectric elements (104).

Figure 6:
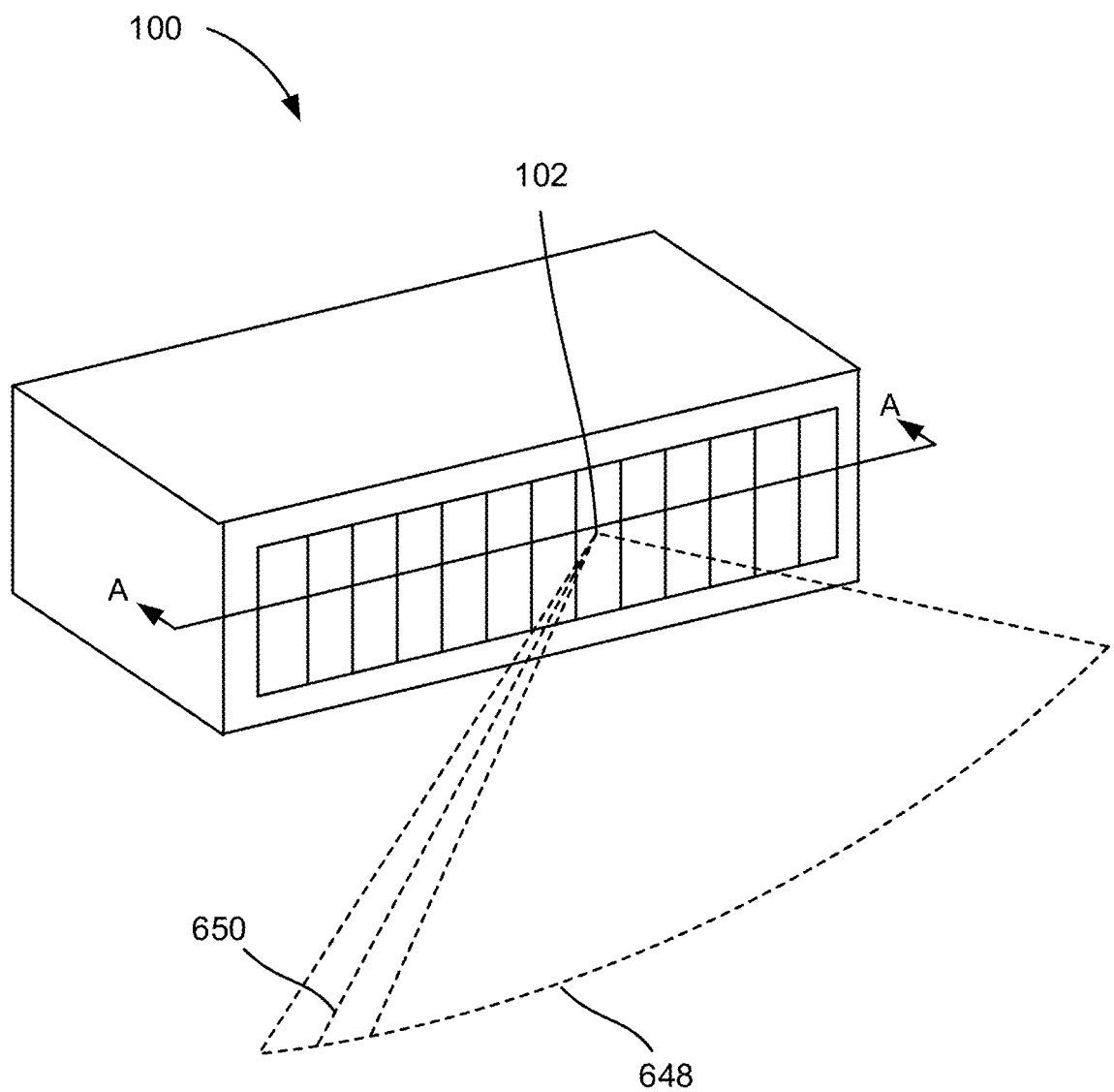
FIG. 6 is an isometric view of an imaging device and scan lines of a frame, according to an example of the principles described herein.

FIG. 6 is an isometric view of an imaging device (100) and scan lines (650) of a frame (648), according to an example of the principles described herein. A frame (648) refers to a single still image of an organ, or other object to be imaged. The frame (648) may be a cross-sectional line through the object. A frame (648) is made up of individual scan lines (650). That is a frame (648) may be viewed as an image, and a scan line is an individual layer or slice of that image. Depending on the resolution, a particular frame (648) may include different numbers of scan lines (650) ranging from less than a hundred to many hundreds.

To form a frame (648), a transducer (102), using beam forming circuitry, focuses pressure waves of different piezoelectric elements (FIG. 1, 104), for example, those in a particular column (FIG. 5, 542) to a particular focal point. The reflected signals collected by these piezoelectric elements (FIG. 1, 104) are received, delayed, weighted, and summed to form a scan line (650). The focal point of interest is then changed based on beam-forming technology, and the process repeated until an entire frame (648), consisting of for example 100-200 scan lines (650) is generated.

While particular reference is made to a particular transmission technique, many different transmit techniques may be employed, including achieving multiple focus with a single transmission from multiple channels. Moreover, the operations described in the present specification are also applicable to these multi-focal transmit signaling techniques. Simultaneous multi-zone focusing can be achieved for example using orthogonal quadratic chirp signaling and can help achieve better resolution as a function of depth. As a specific example, chirp signaling sends a coded signal during transmit where many cycles of frequency or phased modulated coded signals are transmitted. The received echo then is processed with a matched filter to compress the received signal. This method has the advantage of coupling in larger energy into the target compared with situations when only 1 or 2 pulses are transmitted. While axial resolution may become worse when transmitting multiple signals, with chirp signaling, because of use of a matched filter in the receiver, axial resolution is largely restored.

Another issue with chirp signaling is that it uses many cycles of transmit pulses which can increase power consumption. However, in one example, the number of pulses used in chirp signaling or other coded waveform signaling can be reduced to lower power when so desired. This could be for example when a temperature of the imaging device (100) is higher than desired or for example when it is determined that there is a need to reduce power consumption. Alternatively, if improved resolution is desired, the number of pulses and the use of multi-zone focal signaling can be used.

Figure 7:
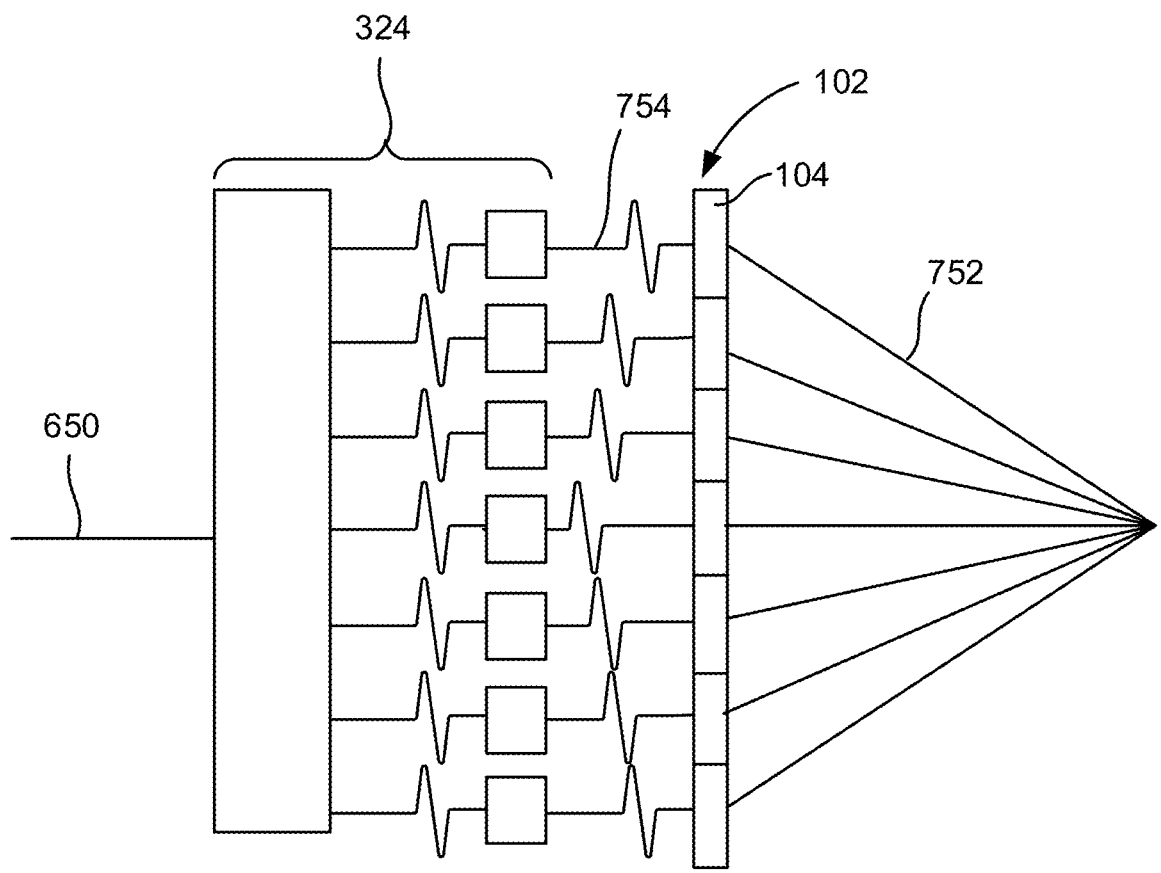
FIG. 7 illustrates the formation of a scan line, according to an example of the principles described herein.

FIG. 7 illustrates the formation of a scan line (650), according to an example of the principles described herein. Specifically, FIG. 7 is a cross-sectional view of one transducer (102) taken along the line A-A from FIG. 6. Specifically, FIG. 7 depicts the piezoelectric elements (104) that make up the transducer (102). In FIG. 7, just one piezoelectric element (104) of a transducer (102) is indicated with a reference number for simplicity. Moreover, note that the piezoelectric elements (104) depicted in FIG. 7 may represent a top piezoelectric element (104) of a column (FIG. 5, 542) with other piezoelectric elements (104) extending into the page. FIG. 7 also depicts circuitry that may be found in the controller (324) to form a scan line (650).

Note also that for simplicity FIG. 7 only depicts seven piezoelectric elements (104), and seven respective columns (FIG. 5, 542). However as described above a transducer (102) may include any number of piezoelectric elements (104), for example, 128 columns (FIG. 5, 542), with each column (FIG. 5, 542) having 32 piezoelectric elements (104) disposed therein.

To form a scan line (650), signals (752) are received from a number of piezoelectric elements (104), for example from each piezoelectric element (104) in a column (FIG. 5, 542). In some examples, signals for piezoelectric elements (104) in a column (FIG. 5, 542) may be combined into a composite signal (754) which is passed to the controller (324). As each composite signal (754) is received at a different time due to different transmission lengths, the controller (324) delays each composite signal (754) such that they are in phase. The controller (324) then combines the adjusted signals to form a scan line (650). Additional detail regarding the processing of received signals (754) by the controller (324) are presented in later figures.

As described above, a frame (FIG. 6, 648) of an image is formed of many scan lines (650), often 128 or more. These scan lines (650) cover the area to be imaged. The time to collect and combine the scan lines (650) into a frame (FIG. 648) defines the quality of the video, in terms of the frame rate, of an object to be imaged. For example, assuming the example of scanning a heart, and assuming the heart is 20 cm below the transducer (102) surface, an ultrasound waveform takes approximately 130 microseconds (us) to travel to the heart, assuming sound travels at 1540 m/s in tissue. The signal is then reflected from the heart and takes another 130 microseconds to reach the transducers (102) for a total transit time of 260 microseconds. Using N receive channels (FIG. 1, 108), for example 128 channels, one scan line (650) is formed by transmitting from 128 transmit channels (FIG. 1, 108) driving 128 columns (FIG. 5, 544) of piezoelectric elements (FIG. 1, 104) and receiving from all 128 columns (FIG. 5, 544) and processing the signals as indicated in FIG. 7. Assuming 128 scan lines (650) per frame (FIG. 6, 648), the maximum frame rate is around 30 fps.

In some examples, 30 fps may be sufficient, for example with livers and kidneys. However, to image moving organs, such as a heart, a higher frame rate may be desired. Accordingly, the imaging device (FIG. 1, 100) may implement parallel beamforming where multiple scan lines (650) can be formed at the same time. As multiple scan lines (650) can be formed at a time, the effective frame rate may be increased. For example, if four scan lines (650) could be formed at the same time, then the effective frame rate may go up to 120 fps. Parallel beamforming may be performed at the FPGAs (FIG. 3, 326) of the imaging device (FIG. 1, 100).

In some examples, the selective powering down of receive and/or transmit channels (FIG. 1, 106, 108) may be affected by parallel beam forming operations. For example, using parallel beam forming a frame rate of 120 fps may be achievable. However, if 30 fps is good enough, the receive channels (FIG. 1, 108) can be enabled ¼ of the time, cutting down power consumption by a factor of 4 or somewhat less than 4, taking into account some requirements that are not amenable to be completely shut down, but can be placed into a materially lower power state. For example, after a set of 4 scan lines are simultaneously collected, the receive channels (FIG. 1, 108) could be turned off for a period of time, and then turned on again to collect another 4 scan lines simultaneously.

Such techniques can reduce power consumption to for example around 3.3 times less than a starting power consumption value. In other words, the selective powering down of the receive channels (FIG. 1, 108) in an imaging device (FIG. 1, 100) that performs parallel beamforming powers down receive channels (FIG. 1, 108) for a portion of the time such that overall frame rate is maintained. Such an operation does not affect the image quality as imaging artifacts can be digitally corrected with operations that are not power intensive and that can be executed in a display processor that is not located in the probe. That is, data from the imaging device (FIG. 1, 100) in the form of scan lines (650) can be transported to the computing device (FIG. 2, 216) unit using a USB interface and this image processing can be done outside of the imaging device (FIG. 1, 100) where there are less restrictions on temperature rise. Obviously, the amount of scaling is dependent upon the number of parallel beams that are transmitted and received. For example, the scaling may be smaller when using two parallel beams or larger when using 8 parallel beams.

Figure 8:
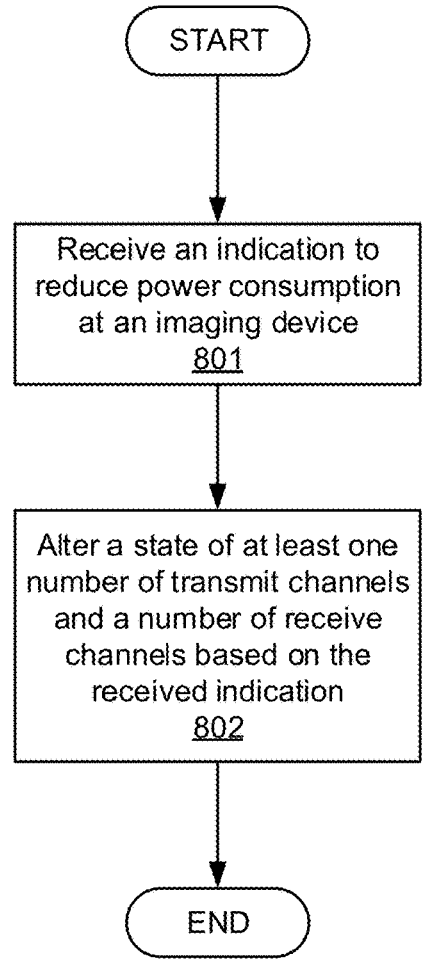
FIG. 8 is a flowchart of a method for selectively altering a number of channels of an imaging device, according to an example of the principles described herein.

FIG. 8 is a flowchart of a method (800) for selectively altering a number of channels (FIG. 1, 106, 108) of an imaging device (FIG. 1, 100), according to an example of the principles described herein. According to the method (800), an indication is received (block 801) that power consumption should be reduced within the imaging device (FIG. 1, 100). Such an indication may come in a variety of forms. For example, the temperature sensors (FIG. 5, 546) disposed on the transducers (FIG. 1, 102) or temperature sensors (FIG. 5, 546) disposed at other locations may indicate that temperatures within the imaging device (FIG. 1, 100) are above a threshold amount.

In another example, the indication may be that a low-resolution imaging operation is being carried out. For example, low frame rate imaging operations may be carried out for certain organs that are relatively stationary. A low frame rate allows shutting down many circuits most of the time as explained earlier, thus saving power and reducing temperature in the imaging device (FIG. 1, 100). Accordingly, in some examples receiving (block 801) the indication includes receiving a user input that an organ that is mostly stationary is going to be imaged.

In another example, the indication may be that the imaging device (FIG. 1, 100) is going to be used in a search mode. During a search mode, high resolution images may not be needed as a user is merely attempting to locate a particular organ or component within an organ. After the organ is identified, the user may then desire higher resolution output. Accordingly, in this example receiving (block 801) the indication includes receiving a user input that the imaging device (FIG. 1, 100) is in a low power mode, such as a search mode. The low power mode is readily functional with lower resolution compared to higher resolution in a high-power mode because a smaller number of channels used in the low-resolution mode may be sufficient and parameters of the channel can be programmed to reduce their signal to noise ratio (SNR). Lower SNR also allows lower power operation, for example by reducing the transconductance of low noise amplifiers in the receive channels (FIG. 1, 108).

Responsive to the indication, a state of at least one transmit channel (FIG. 1, 106) or at least one receive channel (FIG. 1, 108) is altered (block 802). For example, a receive channel (FIG. 1, 108), or multiple receive channels (FIG. 1, 108) may be powered down. In another example a receive channel (FIG. 1, 108) or multiple receive channels (FIG. 1, 108) may be placed in a low power state by, among other things, lowering a transconductance of amplifiers in the receive channels (FIG. 1, 108). Still further, a transmit channel (FIG. 1, 106), or multiple transmit channels (FIG. 1, 106) may be powered down. In yet another example, a transmit channel (FIG. 1, 106) or multiple transmit channels (FIG. 1, 106) may be placed in a low power state. Specifically, regarding the transmit channel (FIG. 1, 106), placing the transmit channel(s) (FIG. 1, 106) in a low power state may include sending a voltage pulse with a lesser magnitude or using a lower number of elements in the transmit channel (FIG. 1, 108).

Such alterations (block 802) may be for an entire imaging cycle or for portions of an imaging cycle. For example, a subset of the receive channels (FIG. 1, 108) and/or transmit channels (FIG. 1, 108) may be powered down while others remain active. Doing so may reduce the frame rate or resolution of the resulting images as a result of the powered down channels not contributing to the formation of scan lines (FIG. 6, 650). However, such a reduction in image quality and frame rate may be acceptable based on the object to be imaged.

In another example, the transmit channels (FIG. 1, 106) and/or receive channels (FIG. 1, 108) may be deactivated for just a portion of the time. For example, for a portion of the formation of an individual scan line (FIG. 6, 650). An example of such is provided below in connection with FIG. 9. Accordingly, the method (800) provides a way for the customized use of an imaging device (FIG. 1, 100) to ensure performance characteristics in line with the intended imaging operation and to ensure the temperature stays within threshold ranges.

Figure 9:
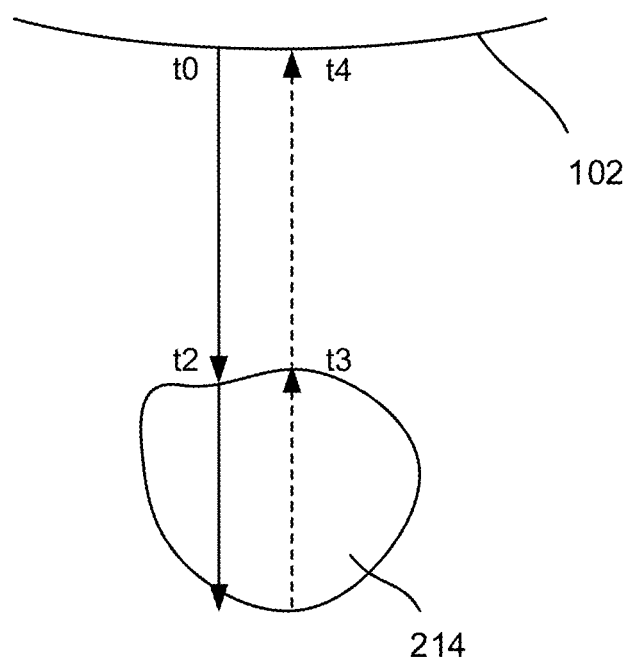
FIG. 9 is a diagram illustrating portions of a scan line forming period during which a receive channel may be altered, according to an example of the principles described herein.

FIG. 9 is a diagram illustrating a portion of time during which a receive channel (FIG. 1, 108) and transmit channel (FIG. 1, 106) may be altered, according to an example of the principles described herein. In this example at time t0 the pressure waves (FIG. 2, 210) are transmitted away from the transducer (102). At the moment the pressure waves (FIG. 2, 210) are transmitted, the respective transmit channels (FIG. 1, 106) may be deactivated or powered down. Thus, as described above, the portion of the imaging cycle, i.e., formation of a scan line (FIG. 6, 650) that a transmit channel (FIG. 1,106) may be shut down corresponds to all time after the pressure wave (FIG. 2, 210) is sent.

In this example, the pressure wave (FIG. 2, 210) reaches the zone of interest at a time t2 and the reflected signal leaves the zone of interest at a time t3 to return to the transducer at a time t4. In other words, the total time for a signal to leave the transducer and return to the transducer is a time t0 to 14. In conventional imaging devices, the receive channel (FIG. 1, 108) may be on for the entire duration t0 to t4. However, as the area of interest is just a portion of that time, then the receive channel (FIG. 1, 108) may be turned off for most of that time. Specifically, the receive channel (FIG. 1, 108) may be powered down for times when the signal is outside of the desired field of view. In this case, if the field of view corresponds to an object (214), then the image is of interest only when ultrasonic waveform is in the position corresponding to times between t2 and t3. Thus, when echo signals corresponding to the time interval between t2 and t3, reach the imaging device (FIG. 1, 100), the receive channels (FIG. 1, 108) are in operation and at other times can either be placed in low resolution or lower power mode or turned off. Thus, the overall power consumption is significantly reduced as the components of the receive channel (FIG. 1, 108) can be entirely powered down or set to a low power state during this time period. This effect is compounded when 1) the receive channel (FIG. 1, 108) is in a low power mode during the time period corresponding to t2-t3 and/or 2) parallel beamforming is used to allow powering down of channels without reducing the frame rate.

As described above, the imaging device (FIG. 1, 100) is connected to/or includes a display device (FIG. 2, 220). In this example, a user interface allows a user to select an organ to be imaged. Doing so presets the imaging device (FIG. 1, 102) 1) to a proper frequency for the pressure waves (FIGS.

2, 210) and 2) to a predetermined field of view for the object. As the image shows up on the display device (FIG. 2, 220), the user may select areas to be imaged, for example by expanding and contracting a window using a finger. The controller (FIG. 3, 324) then converts the selection information from the computing device (FIG. 2, 216) to determine for example the time periods when the receive channel (FIG. 1, 108) can be powered down/placed in a low power state.

In another embodiment, the imaging device (FIG. 1, 100) is first used to guide the operator to obtain a medically relevant issue by helping orient the imaging device (FIG. 1, 100) correctly. This is done for example using artificial intelligence techniques leveraging machine learning. The algorithms guide the user to orient the image in the proper orientation for the desired view of the organ (FIG. 2, 214) being imaged. After the proper orientation is obtained, then the actual imaging session can start at a relevant resolution. However, during the orientation and guidance session, high resolution is not required and therefore, the imaging device (FIG. 1, 100) can be set to a lower power, lower resolution mode, saving power for the overall imaging session.

Figure 10:
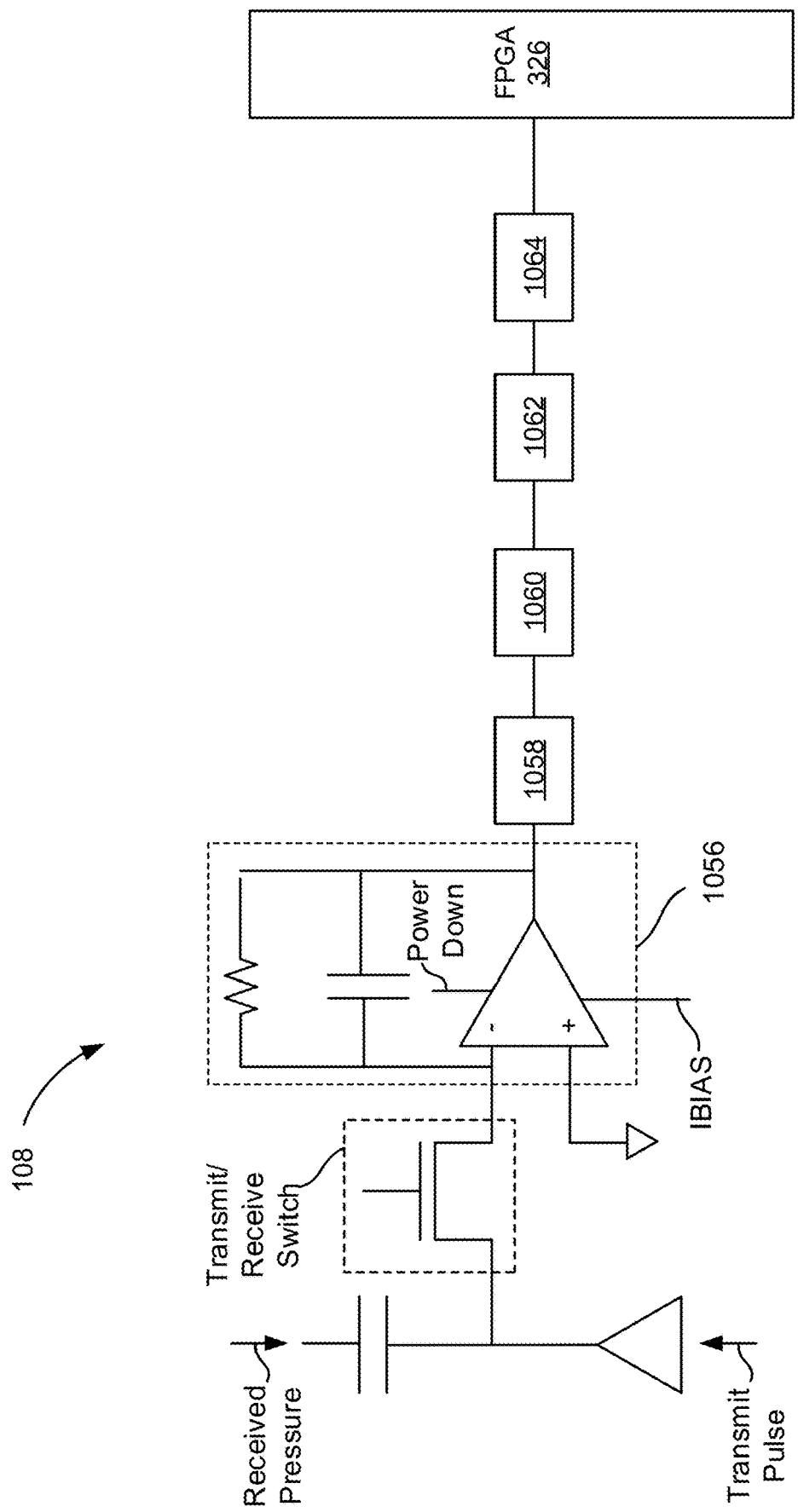
FIG. 10 depicts a receive channel, according to an example of the principles described herein.

FIG. 10 depicts a receive channel (108), according to an example of the principles described herein. The receive channel (108) is coupled to a piezoelectric element (FIG. 1, 104) to receive the reflected pressure wave (FIG. 2, 210). FIG. 10 also depicts the connection between the piezoelectric element (FIG. 1, 104) and the transmit channel (FIG. 1, 106). In one example, the transmit channel (FIG. 1, 106) goes towards a high impedance during a receive operation at the node where the received pressure and transmitted pulse meet.

Figure 11:
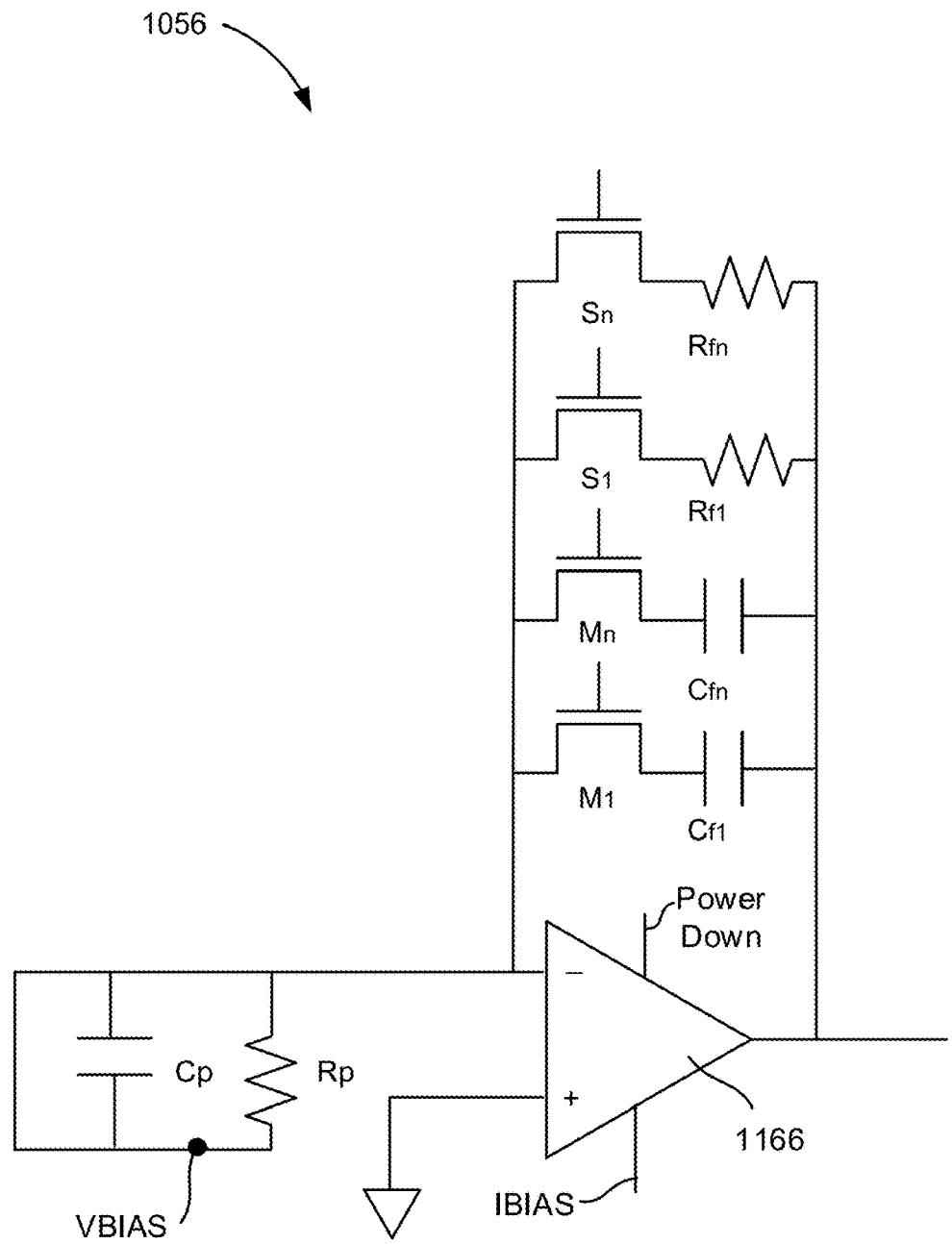
FIG. 11 depicts a low-noise amplifier (LNA) of a receive channel, according to an example of the principles described herein.

In other words, the receive channel (108) receives a reflected pressure waveform from the target to be imaged and the receive channel (108) converts the pressure to electrical voltage. Specifically, the reflected pressure wave is converted to an electrical charge in the transducer and this is converted to a voltage by a low noise amplifier (LNA) (1056). The LNA (1056) is a charge amplifier, where charge is converted to an output voltage. In some examples, the LNA (1056) has programmable gain, where the gain can be changed in real time. An example of a LNA (1056) with programmable gain is depicted in FIG. 11.

The LNA (1056) converts charge in the transducer to a voltage output and also amplifies the received echo signal. A switch (transmit/receive switch) connects the LNA (1056) to the transducer in the receive mode of operation.

The output of this LNA (1056) then is connected to other components to condition the signal. For example, a programmable gain amplifier (PGA) (1058) adjusts the magnitude of the voltage and provides a way to change the gain as a function of time and may be known as a time gain amplifier. As the signal travels deeper into the tissue, it is attenuated. Accordingly, a larger gain is used to compensate, which larger gain is implemented by the TGC. The bandpass filter (1060) operates to filter out noise and out of band signals. An analog to digital converter (ADC) (1062) digitizes the analog signal to convert the signal to the digital domain such that further processing can be done digitally. Data from the ADC (1062) is then digitally processed at a demodulation unit (1064) and passed to the FPGA (326) to generate the scan line (FIG. 6, 650) as depicted in FIG. 7. In some implementations, the demodulation unit (1064) can be implemented elsewhere, for example in the FPGA. The demodulation unit frequency-shifts the carrier signal to baseband with two components in quadrature (I and Q), for further digital processing. In some examples, the analog to digital converter (ADC) (1062) may implement a successive-approximation-register (SAR) architecture to reduce latency of the ADC (1062). That is, as the ADC (1062) is turned off and on repeatedly, it needs to have little to no latency so as to not delay signal processing following turning on.

As described, components of the receive channel (108) may be turned off, or set to a lower power mode to conserve power. That is, significant amounts of power are consumed in the LNA (1056), PGA (1058), ADC (1062) and other digital processing components. In one example, an imaging device (FIG. 1, 100) includes 128 receive channels (108). The power consumption using all 128 receive channels (108) to produce a high number of scan lines (FIG. 6, 650) can cause a large amount of power consumption. As one specific example, presume an LNA (1056) consumes 10 mW, an ADC (1062) consumes 40 mW, and demodulation, I/Q conversion consumes another 10 mW. In this example, each receive channel (108), not counting the power consumed by digital processing, consumes 60 mW. Incorporating the digital processing which is used to form scan lines (FIG. 6, 650) using a low power FPGA (326), for a 128 channel (108) implementation is around 12 W in the FPGA (326), of which around 9 W would be in computational matters and rest in overhead in I/O and static losses. Thus for 128 receive channels (108) power consumed will be in this example almost 20 W. Such a power level is technically impractical to support in a handheld imaging device (FIG. 1, 100). Power numbers in the 2-less than 10 W are more reasonable power levels. Accordingly, by reducing the number of receive channels (108) by half results in a corresponding halving of the power consumed. The reduction in power not only improves battery life, but also affects the temperature of the imaging device (FIG. 1, 100). Note that while FIG. 10 depicts particular components in the receive channel (108), the receive channel (108) may include other components that may similarly be placed in low power or powered down states.

Other than changing the number of channels, other parameters can also be configured to materially reduce the power, such as shutting down (or lowering power) of all channels most of the time by using parallel beam forming to boost the frame rate and then shutting down circuits for time consistent to targeted frame rates.

FIG. 11 depicts a low-noise amplifier (LNA) (1056) of a receive channel (FIG. 1, 108), according to an example of the principles described herein. In the example depicted in FIG. 11, a bank of capacitors $C_{f1}$-$C_{fn}$ are electronically selected by turning on switches $M_1$-$M_n$ and are connected across an operational amplifier (1166). $R_{f1}$-$R_{fN}$ are a bank of resistors that are also electronically programmed by turning on switches $S_1$-$S_N$. FIG. 11 also depicts a bias current input (IBIAS). IBIAS may be generated by the circuit depicted in FIG. 12. IBIAS is used to change the transconductance of the LNA (1056), where higher current level reduce noise level. Additionally, a digital input indicating power down also is used to shut down the LNA (1056). To achieve fast power up, IBIAS needs to be established quickly with an example implementation shown in FIG. 12.

Figure 12:
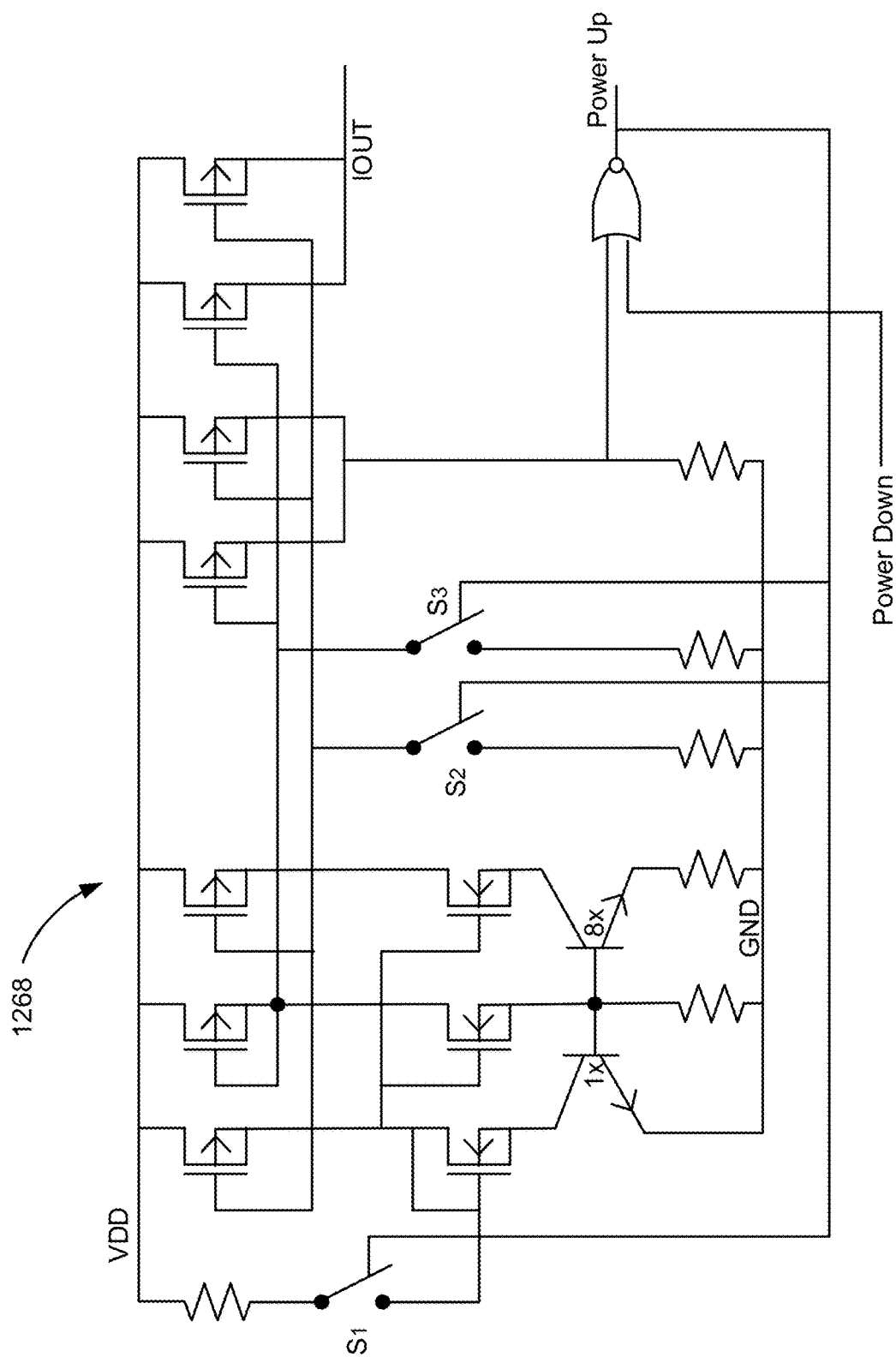
FIG. 12 is a circuit diagram of a fast power-up biasing circuit, according to an example of the principles described herein.

That is, FIG. 12 is a circuit diagram of a fast power-up biasing circuit (1268), according to an example of the principles described herein. As described above, when the receive channel (FIG. 1, 108) is powered on and off multiple times during operation, it is crucial that components can be rapidly turned on and off in order to ensure proper dissipation of heat and proper operation of the imaging device (FIG. 1, 100). In this example the IOUT terminal is coupled to the bias current input, IBIAS, of the LNA (FIG. 10, 1056) so as to ensure that the LNA (FIG. 10, 1056) is quickly powered up. That is, in order to implement the imaging device (FIG. 1, 100) effectively, the components in the signal path such as LNA (FIG. 10, 1056) and the ADC (FIG. 10, 1064) in each receive channel (FIG. 1, 108) should be able to shut down in around hundreds of nanoseconds and also should be powered up in around 1 us. The fast power-up biasing circuit (1268) depicted in FIG. 12 is one example of providing such a quick power-up and shutdown. The biasing circuit (1268) depicted in FIG. 12 exhibits very fast turn on and turn off times. If the Power Down signal is high, then Power Up bootstrap is low, turning off switches S1-S3, so that they do not conduct current, thus reducing the value of IOUT so as to effectively turn it off. When Power Down goes to low, i.e., we wish to power up the LNA (1056), both inputs of the NOR gate are at low and this creates a high logic signal at Power Up bootstrap. This turns on the switches S1-S3 restoring current to IOUT rapidly. IOUT is a current output whose value is copied in other circuits such as the LNA (FIG. 10, 1056) to power these circuits. The value of IOUT is close to zero during power down and has a higher value, typically in the tens or hundreds of uA, during power up.

FIGS. 13-17 illustrate the fabrication of a piezoelectric element (FIG. 1, 104), according to an example of the principles described herein. In some examples, the piezoelectric elements (FIG. 1, 104) have a suspended membrane associated with them that vibrates at a center frequency and several other frequencies when exposed to stimulus at that frequency and as such behave like resonators. There is a selectivity associated with these resonators, known as a Q factor. For ultrasound imaging devices (FIG. 1, 102), Q may be usually designed to be low (close to one) and achieved by a combination of design of the pixels and loading applied to the pixels in actual use. The loading may be provided by application of a layer of RTV or other material to the top face of the piezoelectric elements (FIG. 1, 104), where the loading may facilitate closer impedance matching between the transducer surface emitting and receiving the pressure waves and the human body part being imaged. The low Q and the well-matched center frequency may allow the line element to essentially act like a line imaging element with substantially one center frequency. Loading may also include a matching layer below the transducers, where the emitted waveform is absorbed by an acoustic absorber.

Figure 13:
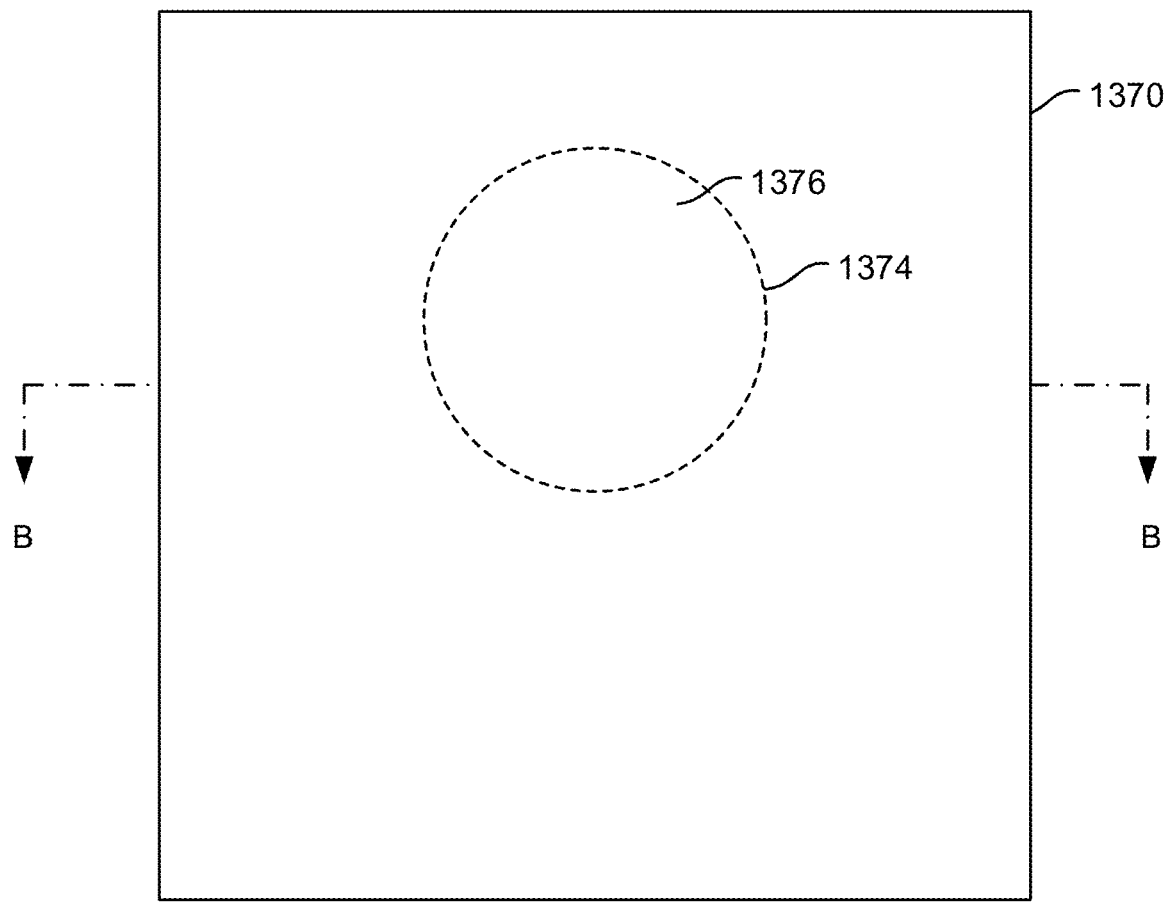
FIGS. 13-17 illustrate the fabrication of a piezoelectric element, according to an example of the principles described herein.
Figure 14:
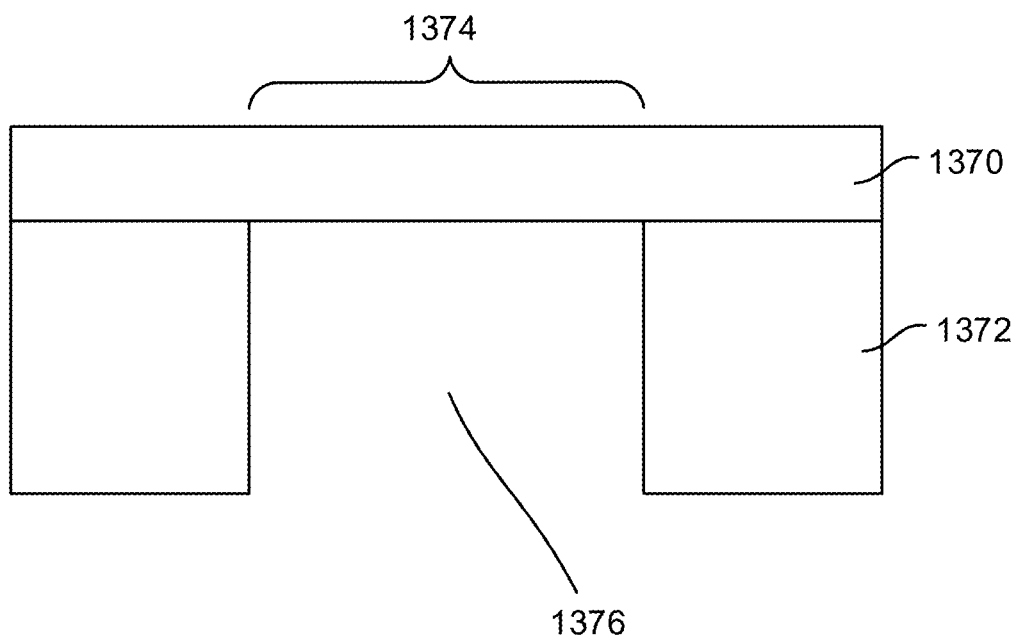

FIG. 13 shows a top view of a membrane (1374) disposed on a substrate (1372) and FIG. 14 shows a cross sectional view of the membrane (1374) and substrate (1372), taken along the line B-B in FIG. 13. The substrate (1372) may correspond to the transceiver substrate (540) in FIG. 5. As depicted, a membrane layer (1370) may be deposited on the substrate (1372) and a cavity (1374) may be formed to remove a portion of the substrate (1372), to thereby form the membrane (1374) that may vibrate relative to the substrate (1372) in the vertical direction. The cavity (1376) may be formed by conventional wafer processing techniques, such as etching, for example deep reactive ion etching (DRIE). The substrate (1372) may be formed of the same material as the membrane layer (1370). In another example, the substrate (1372) may be formed of a different material from the membrane layer (1370). The cavity (1376) may be formed after the other components, of the piezoelectric element (FIG. 1, 104), are formed. While FIG. 13 and others depict the membrane (1374) as having a circular projection area, the membrane (1374) may have other suitable geometrical shape.

Figure 15:
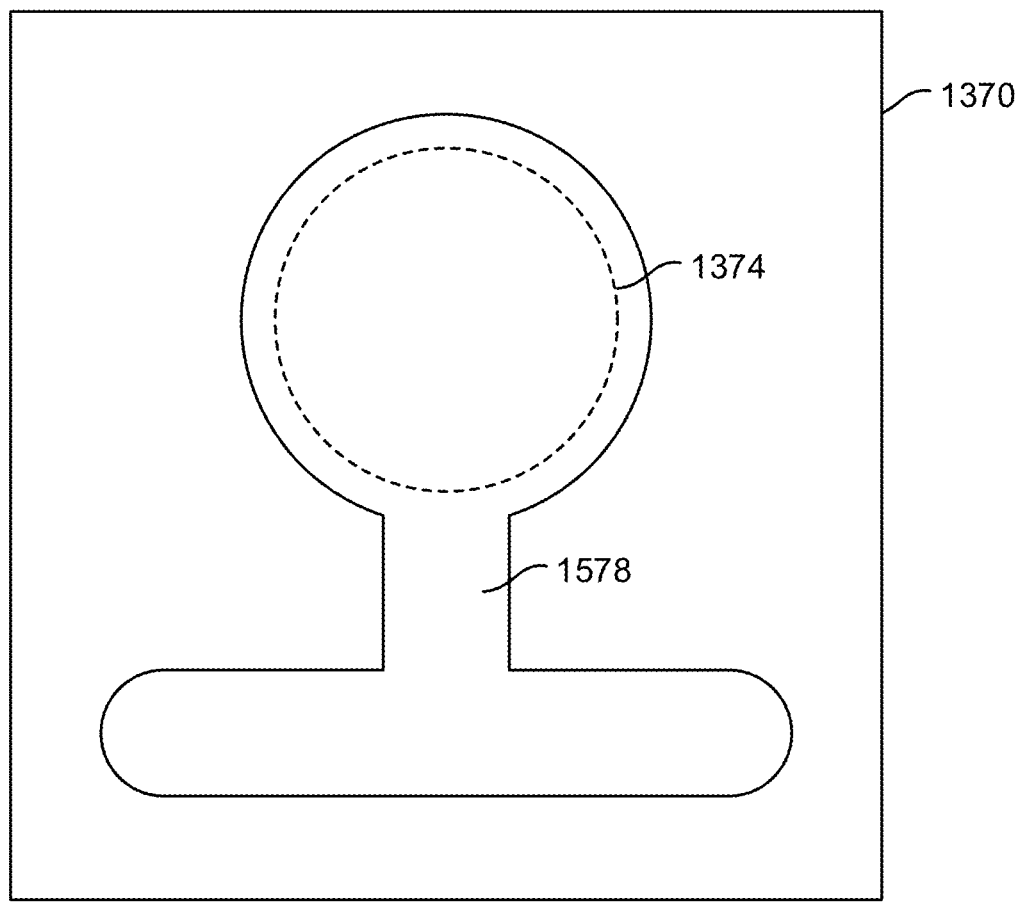
Figure 16:
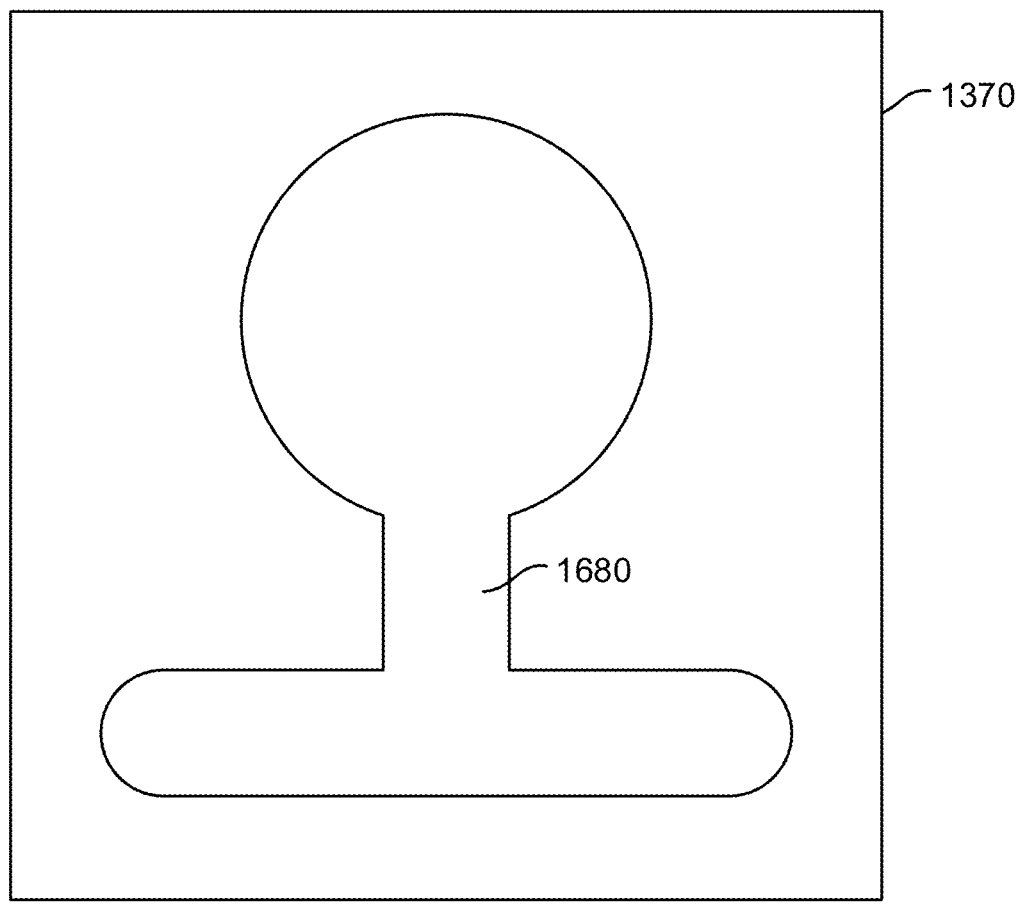

FIG. 15 shows a top view of a bottom electrode (1578) disposed on the membrane layer (1370) and arranged over the membrane (1374) according to an example of the principles described herein. FIG. 16 shows a top view of a piezoelectric layer (1680) disposed on the bottom electrode (FIG. 15, 1578) according to an example of the principles described herein. In some examples, the piezoelectric layer (1680) may have the similar projection area as the bottom electrode (1578) so that the piezoelectric layer (1680) may cover the entire portion of the bottom electrode (1578).

Figure 17:
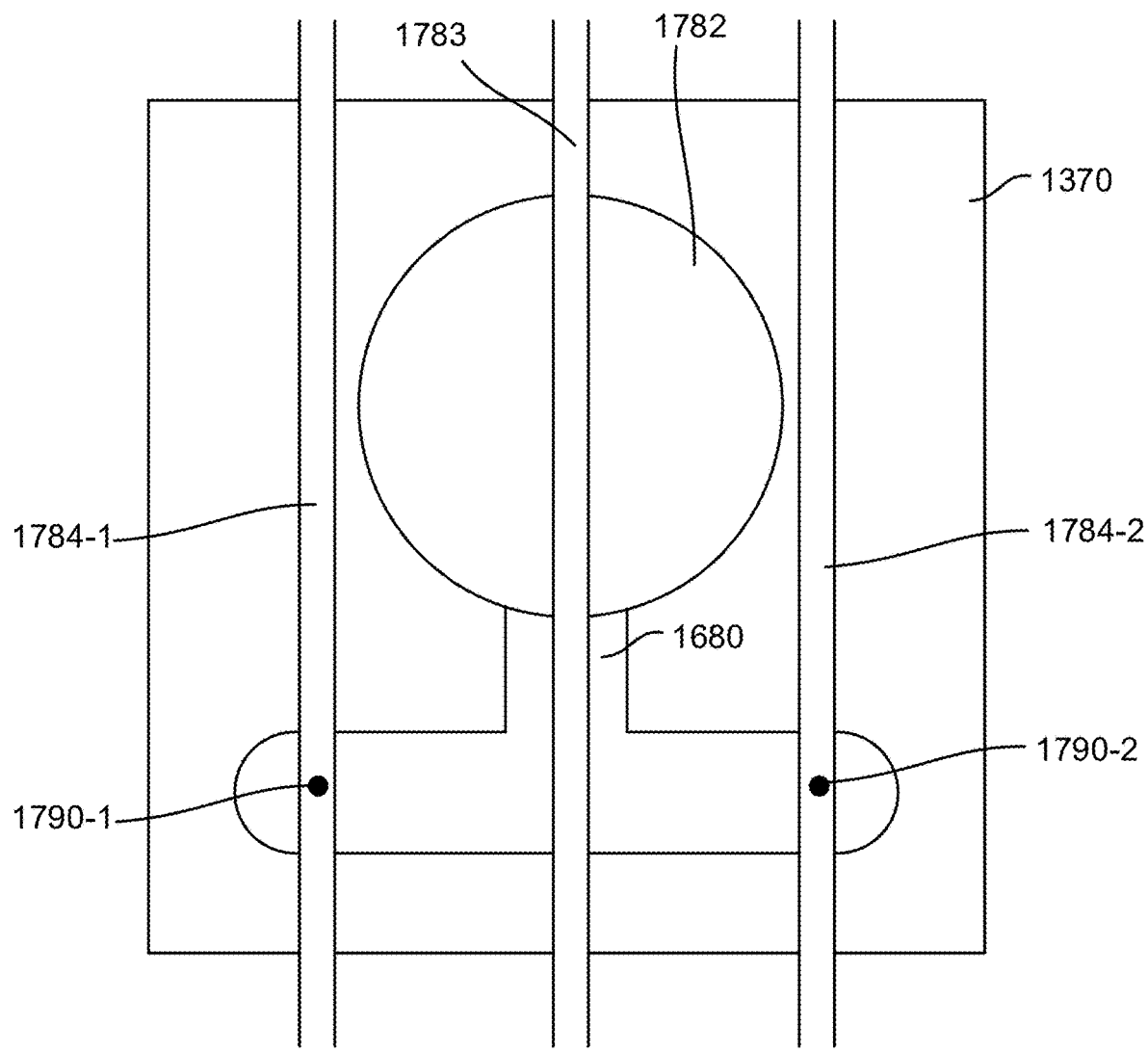

FIG. 17 shows a top view of a piezoelectric element according to an example of the principles described herein. As depicted, a top electrode (1782) may be disposed on the piezoelectric layer (1680) and arranged over the membrane (FIG. 13, 1374). In some examples, a top electrode conductor (1783) may be disposed on and electrically coupled to the top electrode (1782), while bottom electrode conductors (1784-1) and (1784-2) may reach the bottom electrode (1578) through one or more vias (1790-1, 1790-2). In this example, the top electrode (1782), the piezoelectric layer (1680) and the bottom electrode (1578) may form a two terminal piezoelectric element and the membrane (FIG. 13, 1374) may vibrate when an electrical voltage is applied across the top and bottom electrodes (1782, 1578). The electrical charge may be developed in the top and bottom electrodes (1782, 1578) when the membrane (FIG. 13, 1374) is deformed by a pressure wave (FIG. 2, 210) during a receive mode/process.

Figure 18:
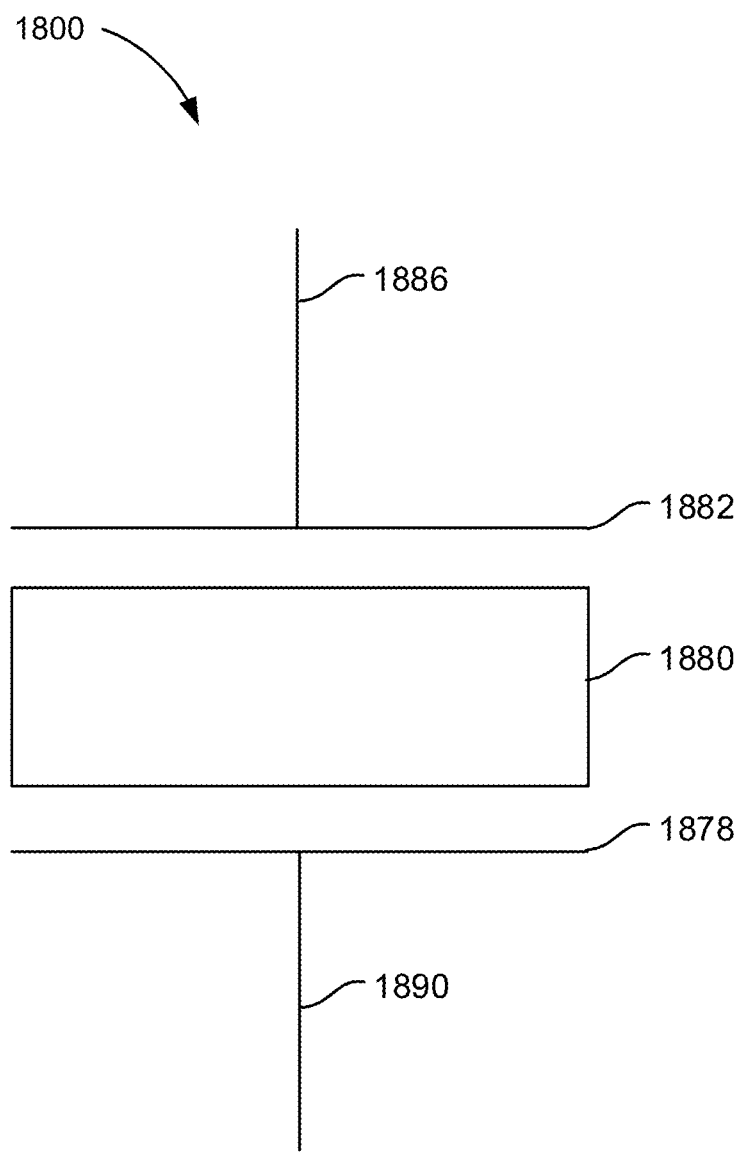
FIG. 18 is a schematic diagram of a piezoelectric element, according to an example of the principles described herein.

FIG. 18 is a schematic diagram of a piezoelectric element (1800), according to an example of the principles described herein. As depicted, a piezoelectric layer (1880) may be disposed between a first electrode (1882) and a second electrode (1878). The first electrode (1882) may be connected to a ground or a DC bias via a first conductor (1886) and the second electrode (1878) may be connected to an electrical circuit (not shown in FIG. 18) through a second conductor (1890).

In the conventional piezoelectric elements, the piezoelectric layer is thick, approaching around 100 μm and typically an AC voltage of +100 to −100 V across the piezoelectric layer is required to create an ultrasonic pressure wave of sufficient strength to enable medical imaging. The frequency of this AC drive signal is typically around the resonating frequency of the piezoelectric structure, and typically above 1 MHz for medical imaging applications. In conventional systems, the power dissipated in driving the piezoelectric element is proportional to $f*C*V^2$, where C is capacitance of the piezoelectric element and V is the maximum voltage across the piezoelectric layer and f is frequency with which drive is being done. Typically, when transmitting pressure waves, multiple piezoelectric lines are driven together with somewhat different phase delays to focus the pressure waves or to steer a propagation direction of the pressure waves. The simultaneous drive of multiple piezoelectric lines causes the temperature at the surface of the piezoelectric elements to rise. In general, it is highly desirable not to exceed a certain threshold temperature, so as not to injure the subject being imaged. This limits the number of lines that can be driven and the time period for which they can be driven and the voltage they can be driven at In the piezoelectric element (1800) of the present specification, the piezoelectric layer (1880) may be much thinner, for example 1-5 um thick . . . This large reduction in thickness may enable the use of lower voltage drive signals for the piezoelectric element (1800), where the voltage is lowered approximately by the amount by which the thickness of the piezoelectric layer (1880) is lowered to maintain the similar electric field strength. For example, the voltage potential across the two electrodes (1882) and (1878) may range from around 1.8 V to 40 V peak to peak. The capacitance of the piezoelectric element (1800) may increase due to the reduction in thickness of the piezoelectric layer (1880) for similar piezoelectric material. For instance, when the drive voltage is decreased by a factor of 10 while the thickness of the piezoelectric layer (1880) is also decreased by a factor of 10, the capacitance increases by a factor of 10 and the power dissipation decreases by a factor of 10. This reduction in power dissipation also reduces heat generation and temperature rise in the piezoelectric element (1800). Thus, using lower drive voltages and thinner piezoelectric layers, compared to the conventional piezoelectric elements, the temperature of the piezoelectric element (1800) surface may be lowered. Alternately, for a given temperature, more piezoelectric elements (1800) may be driven simultaneously to illuminate the larger target area, compared to the conventional piezoelectric elements. This may allow faster scanning of the target, especially if multiple emissions are needed to scan the entire portion of the target to form one image. A target area may be scanned with multiple emissions using different steering angles and the obtained image data may be combined to obtain a higher quality image.

Transducers may have large apertures and it may be desirable to operate on the entire aperture. However, the power consumption maybe excessive if drive voltages are high for bulk piezoelectric elements. Therefore, only a portion of the aperture is transmitted and received, followed by other operations using the rest of the aperture. Compared to the conventional bulk piezoelectric elements, the piezoelectric elements (1800) of the present specification provide the ability to drive more piezoelectric elements simultaneously at a lower voltage for a given power level which allows more coverage of the transducer aperture per emission, minimizing the number of emissions needed to cover the entire aperture, thus increasing frame rates. A frame rate measures how many times a target is imaged per minute. It is desirable to image at a high frame rate, especially when tissue motion is involved since the moving tissue may make the image blurry. An imaging device (FIG. 1, 100) that operates at a higher frame rate may be able to generate images of enhanced quality, compared to the conventional bulk piezoelectric elements.

Figure 19A:
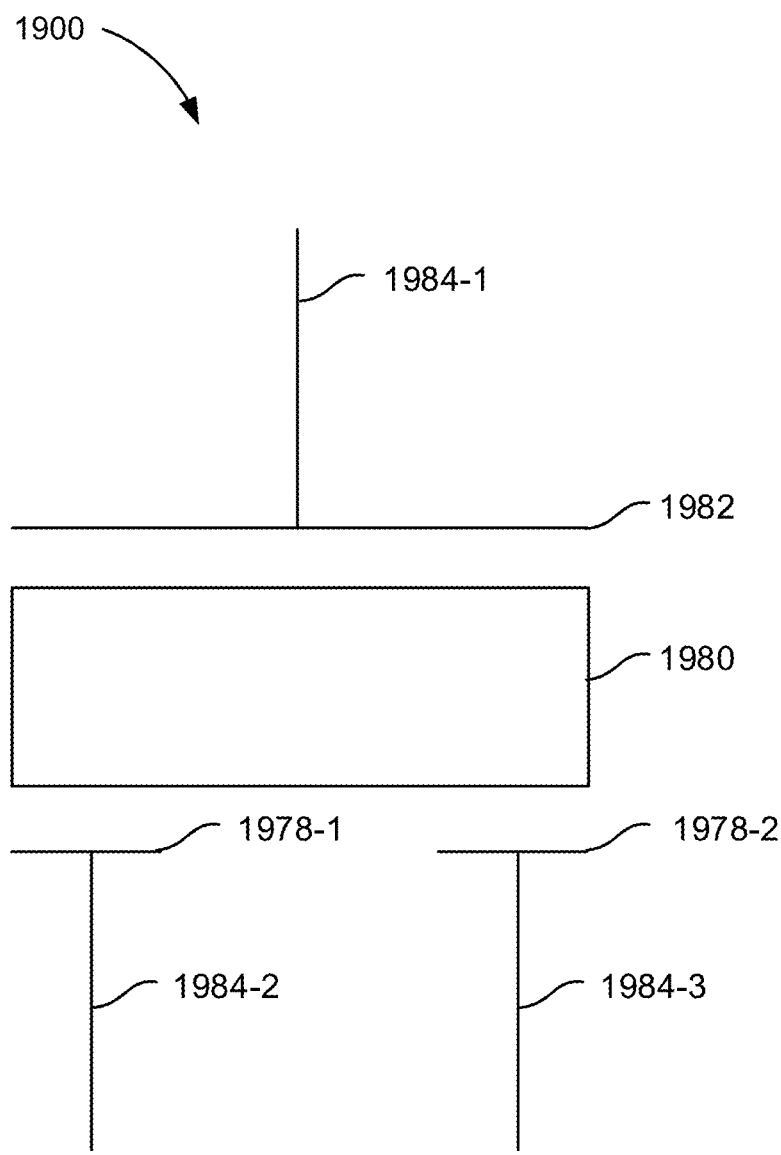
FIG. 19A is a schematic diagram of a piezoelectric element, according to another example of the principles described herein.
Figure 19B:
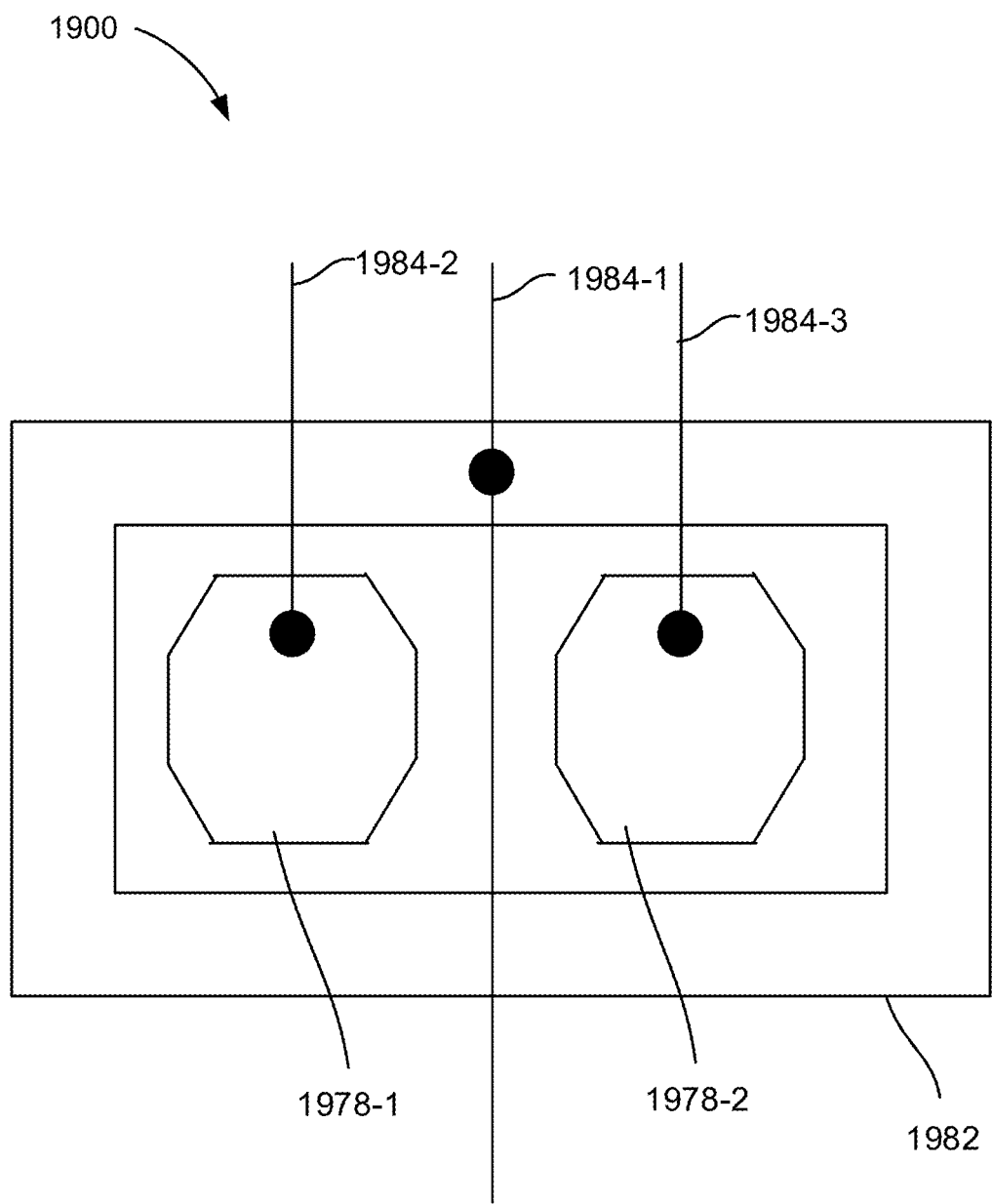
FIG. 19B is a symbolic representation of the piezoelectric element of FIG. 19A, according to an example of the principles described herein.

FIG. 19A is a schematic diagram of a piezoelectric element (1900), according to another example of the principles described herein. FIG. 19B shows a symbolic representation of the piezoelectric element (1900) in FIG. 19A. As depicted, the piezoelectric element (1900) is similar to the piezoelectric element (1800), with the difference that the piezoelectric element (1900) has more than two electrodes. More specifically, the piezoelectric element (1900) may include: a top electrode (1982), a first bottom electrode (1978-1); a second bottom electrode (1978-2); a piezoelectric layer (1980) disposed between the top and bottom electrodes; and three conductors (1984-1), (1984-2), (1984-3) that are electrically coupled to the bottom and top electrodes (1982), (1978-1), (1978-2), respectively. Hereinafter, the terms top and bottom merely refer to two opposite sides of the piezoelectric layer, i.e., the top electrode is not necessarily disposed over the bottom electrode.

The piezoelectric element (1900) depicted in FIG. 19A is particularly helpful to increase sensitivity of transmit and receive operations. For example, when a piezomaterial is manufactured, the dipoles in the piezomaterial are not aligned and for optimal piezo performance, a poling process is implemented where a strong electric field is applied across the piezo film at high temperature (such as 175 deg C.). This establishes the direction of the electric field for later operations. However, if a piezo subelement used for basic transmit and receive operation has a differently poled unit, its sensitivity is enhanced, i.e. For a receive pressure wave, it formed more charge signal on receive operations and for a given transmit voltage drive, more pressure is created. FIG. 19A shows a piezoelectric element (1900) with 3 leads, where a first lead (1984-1) can be grounded during a poling operation, a second lead (1984-2) can be at a high voltage, say positive 15V, and a third lead (1984-3) can be at −15V. Accordingly, an orthogonal electric field is established in the piezoelectric element (1900) during this poling operation. During actual use, the second lead (1984-2) and third lead (1984-3) can be tied to DC bias voltages and act as a virtual ground, while the first lead (1984-1) is used for transmit and receive operations.

While a unimorph piezoelectric element is shown in FIG. 19A purely for the purpose of illustration, in embodiments, a multiplayer piezoelectric element composed of a plurality of piezoelectric sublayers and electrodes can be utilized. In embodiments, the piezoelectric layer (1980) may include at least one of PZT, PZT-N, PMN-Pt, AlN, Sc—AlN, ZnO, PVDF, and LiNiO3.

FIG. 19B is a symbolic representation of the piezoelectric element of FIG. 19A, according to an example of the principles described herein.

Figure 19C:
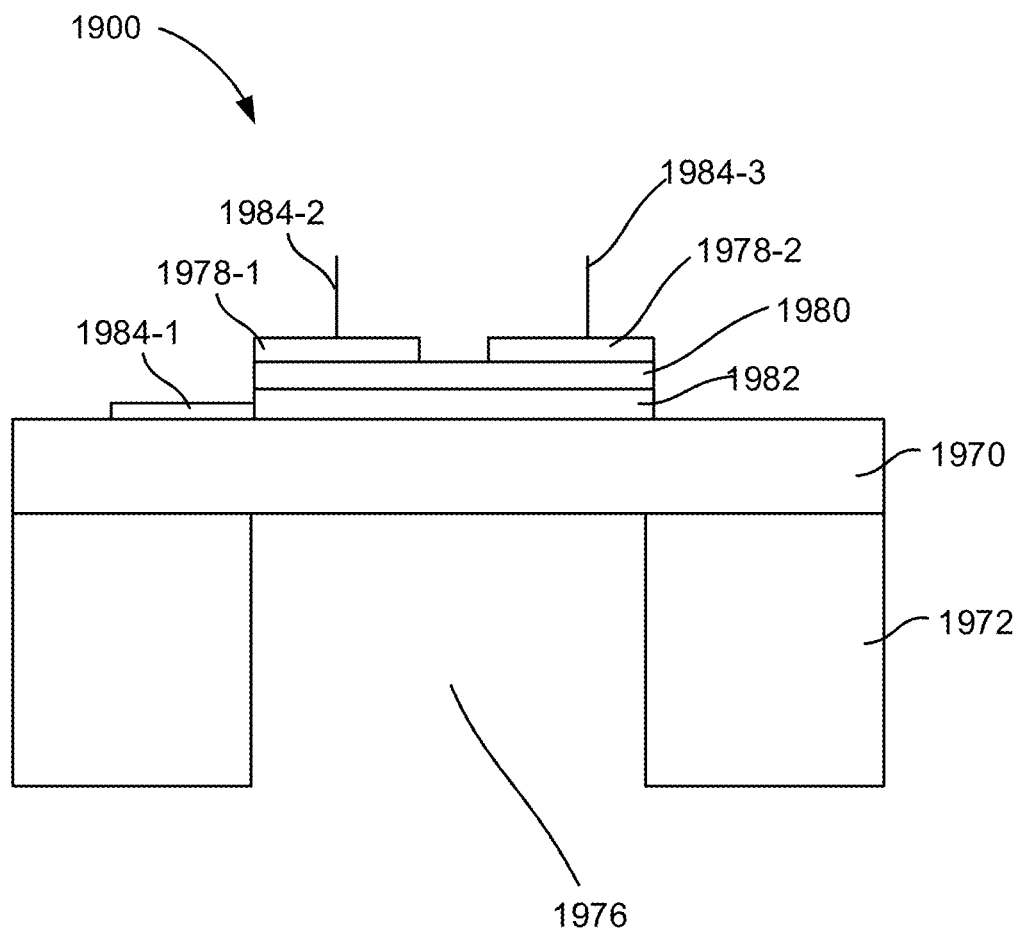
FIG. 19C is a schematic cross sectional view of a piezoelectric element, according to an example of the principles described herein.

FIG. 19C is a schematic cross-sectional view of a piezoelectric element (1900), according to an example of the principles described herein. As depicted, the piezoelectric element (1900) may be disposed on a membrane layer (1970) that is supported by a substrate (1972). A cavity (1976) may be formed in the substrate (1972) to define a membrane. The membrane layer (1970) may be formed by depositing SiO2 on the substrate (1972).

The piezoelectric element (1900) may include a piezoelectric layer (1980) and a first electrode (1982) that is electrically connected to a top electrode conductor (1984-1). The top electrode conductor (1984-1) may be formed by depositing $TiO_2$ and metal layers on the membrane layer (1970).

A first bottom electrode (1978-1) may be grown above the piezoelectric layer (1980) and electrically connected to a first bottom conductor (1984-2). A second bottom electrode (1978-2) may be also grown above the piezoelectric layer (1980) and disposed adjacent to the second bottom conductor (1984-3) but electrically isolated from the first bottom conductor (1984-2). The second bottom electrode (1978-2) and second bottom conductor (1984-3) may be formed by depositing one metal layer on the piezoelectric layer (1980) and patterning the metal layer. In some examples, the projection areas of the electrodes (1984) may have any suitable shape, such as square, rectangle, circle, and ellipse, so on.

The first electrode (1982) may be electrically connected to the conductor (1984-1) using a metal, a via and interlayer dielectrics. In some examples, the first electrode (1982) may be in direct contact with the piezoelectric layer (1980). The second bottom conductor (1978-2) may be deposited or grown on the other side of the piezoelectric layer (1980) with respect to the first electrode (1982).

Figure 19D:
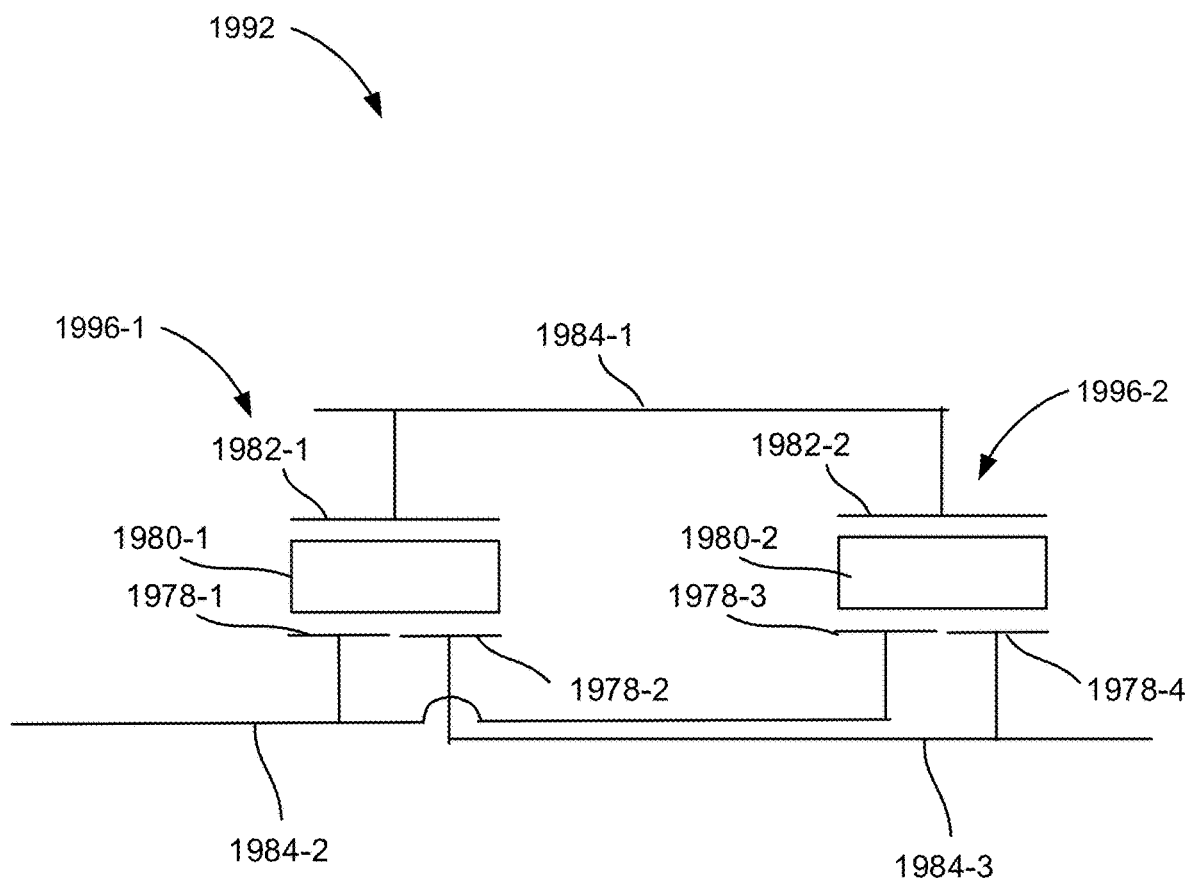
FIG. 19D is a schematic diagram of a piezoelectric element, according to another example of the principles described herein.

FIG. 19D is a schematic diagram of a piezoelectric element (1992), according to another example of the principles described herein. As depicted, the piezoelectric element (1992) may include two sub piezoelectric elements (sometimes referred to as sub elements) (1996-1) and (1996-

2). Each sub element may be a three-terminal device, i.e., it may have one top electrode (1982-1, 1982-2), two bottom electrodes (1978-1, 1978-2) and (1978-3, 1978-4), and one piezoelectric layer (1980-1, 1980-2). The top electrode (1982-1) of the first sub element (1996-1) may be electrically connected to the top electrode (1982-2) of the second sub element (1996-2) by a common top conductor (1984-1). The first bottom electrode (1978-1) of the first sub element (1996-1) may be electrically connected to the first bottom electrode (1978-3) of the second sub element (1996-2) by a first bottom conductor (1984-2). The second bottom electrode (1978-2) of the first sub element (1996-1) may be electrically connected to the second bottom electrode (1978-4) of the second sub element (1996-2) by a second bottom conductor (1984-3). In one example, the piezoelectric element (1992) may be disposed on one membrane or each sub element may be disposed on a separate membrane. It should be apparent to those of ordinary skill in the art that the conductor (1984-1) may be electrically connected to the electrodes (1982-1, 1982-2), using metals, vias, interlayer dielectrics (ILD), so on, in the similar manner as the piezoelectric element illustrated in FIGS. 13-17.

In some examples, the conductor (1984-2) and the conductor (1984-3) may be all grounded (or connected to a DC bias) during active operation of the imaging device (FIG. 1, 100). In some examples, the top electrodes (1982-1, 1982-2) may be driven by a common transmit driver circuit and a common electrical signal, typically a signal waveform around the center frequency of the transducer. For example, if the center frequency is 2 MHz, a sinusoidal waveform or square waveform at 2 MHz is applied to the piezoelectric element (1992). This waveform may cause the piezoelectric element (1992) to resonate at 2 MHz and send out a pressure wave (FIG. 2, 210), from the surface of the transducer The pressure wave (FIG. 2, 210) may be reflected from the target organ to be imaged. The reflected pressure wave may hit the piezoelectric element (1992) which is now connected to a signal receiver. The pressure wave may be converted to the electrical charge in the piezoelectric element (1992) by the piezoelectric layers (1980-1, 1980-2). This charge may be signal processed by amplifiers, filters and eventually digitized by an A/D converter (not shown in FIG. 19D), followed by digital decimators with the data eventually interfaced to FPGAs or Graphical Processing Units (GPUs). These processed signals from multiple piezoelectric elements may be then reconstructed into images. The signal waveform driving the transmit driver can also be a frequency varying signal or a phase varying signal or other complex coded signals, such as chirps or Golay codes.

In one example, the transducer may be a wide bandwidth multimodal device, where the membranes can vibrate at a number of different frequencies simultaneously spread over a wide band, thus creating a wide bandwidth transducer. This operation is valid in both the transmit mode and the receive mode.

Figure 19E:
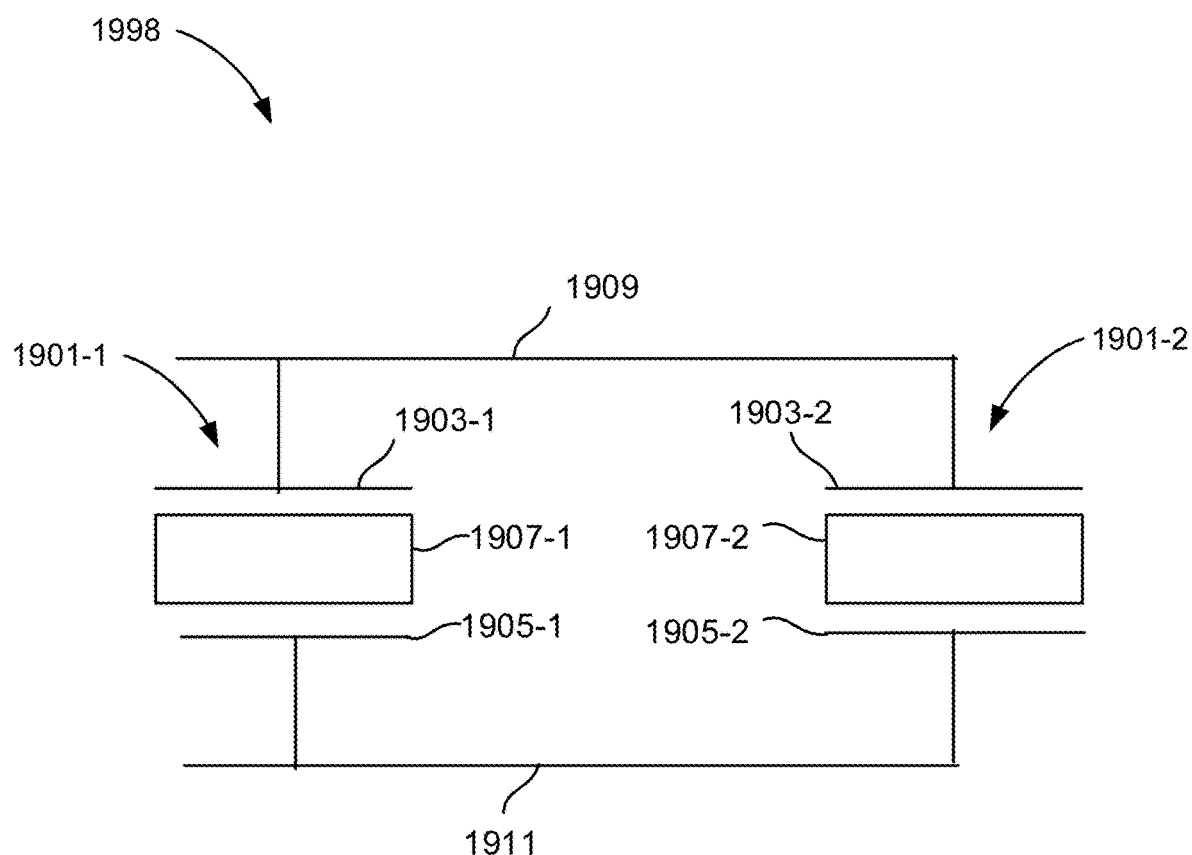
FIG. 19E is a schematic diagram of a piezoelectric element, according to an example of the principles described herein.

While piezoelectric element can exhibit multiple modes of vibration, in some examples, just one mode of vibration is triggered when input stimulus is bandlimited to be less than frequencies of adjacent modes. Further, frequencies generated from a first mode of vibration can be designed to overlap those from the second mode of vibration. Still further, in some examples multiple modes of vibration simultaneously when driven by a wide band frequency input that includes center frequencies FIG. 19E is a schematic diagram of a piezoelectric element (1998), according to an example of the principles described herein. As depicted, the piezoelectric element (1998) may include two sub elements (1901-1, 1901-2). Each sub element (1901) may be a two-terminal device, i.e. it may have one top electrode (1903-1, 1903-2), one bottom electrode (1905-1, 1905-2), and one piezoelectric layer (1907-1, 1907-2). The top electrode (1903-1) of the first sub element (1901-1) may be electrically connected to the top electrode (1903-2) of the second sub element (1901-2) by a common conductor (1909), and the bottom electrode (1905-1) of the first sub element (1901-1) may be electrically connected to the bottom electrode of the second sub element (1901-2) by a common conductor (1911). In some examples, the piezoelectric element (1998) may be disposed on one membrane or each sub element may be disposed on a separate membrane.

In some examples, the sub elements (1901-1, 1901-2) may have different center frequencies and when operated together as a single composite element, may exhibit wider bandwidth, and still operate as a two-terminal device. Note, this wide bandwidth performance can also be achieved with using the structure shown in FIG. 19D, where sensitivity also can be increased using dual polarization technique.

Figure 19F:
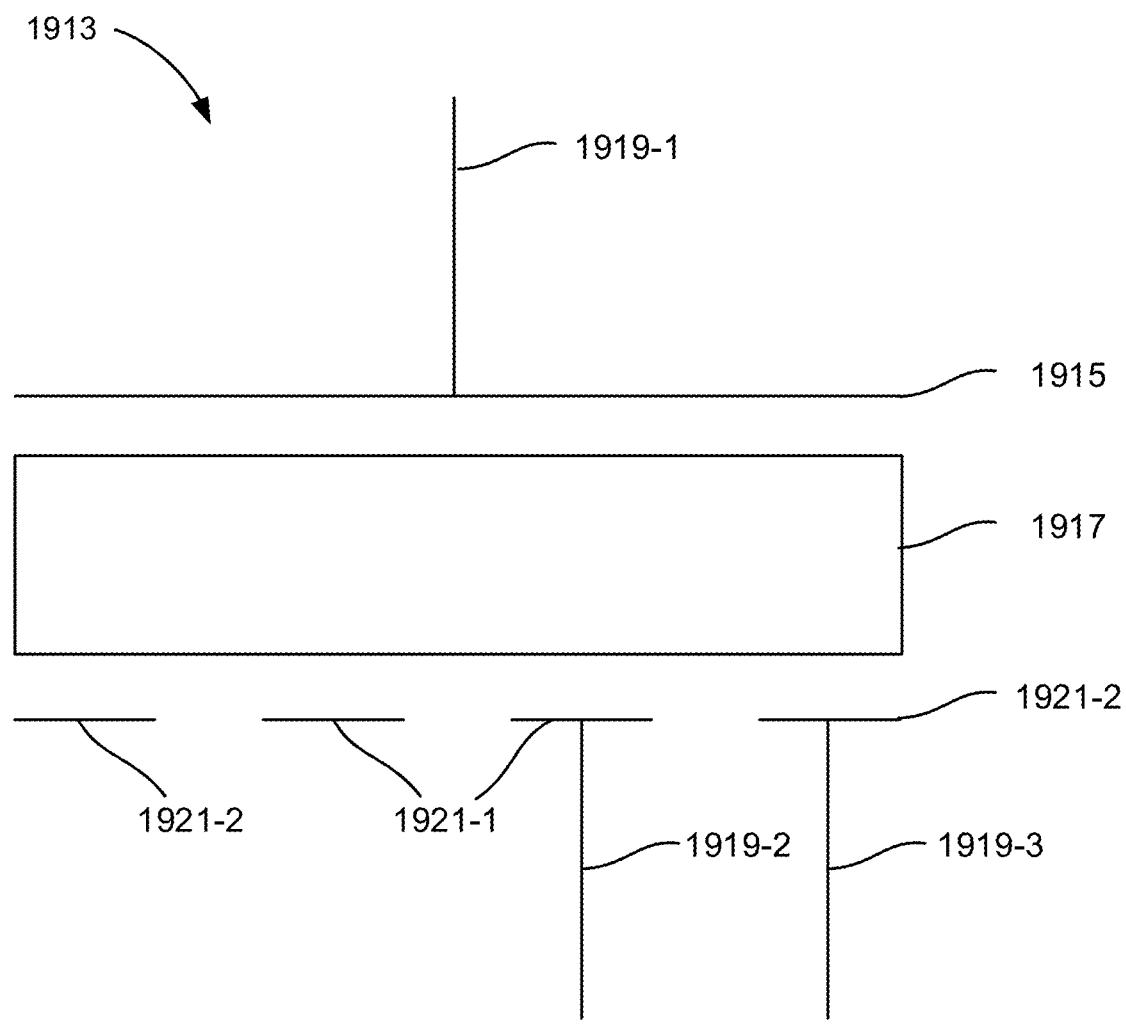
FIG. 19F is a schematic diagram of a piezoelectric element, according to an example of the principles described herein.
Figure 19G:
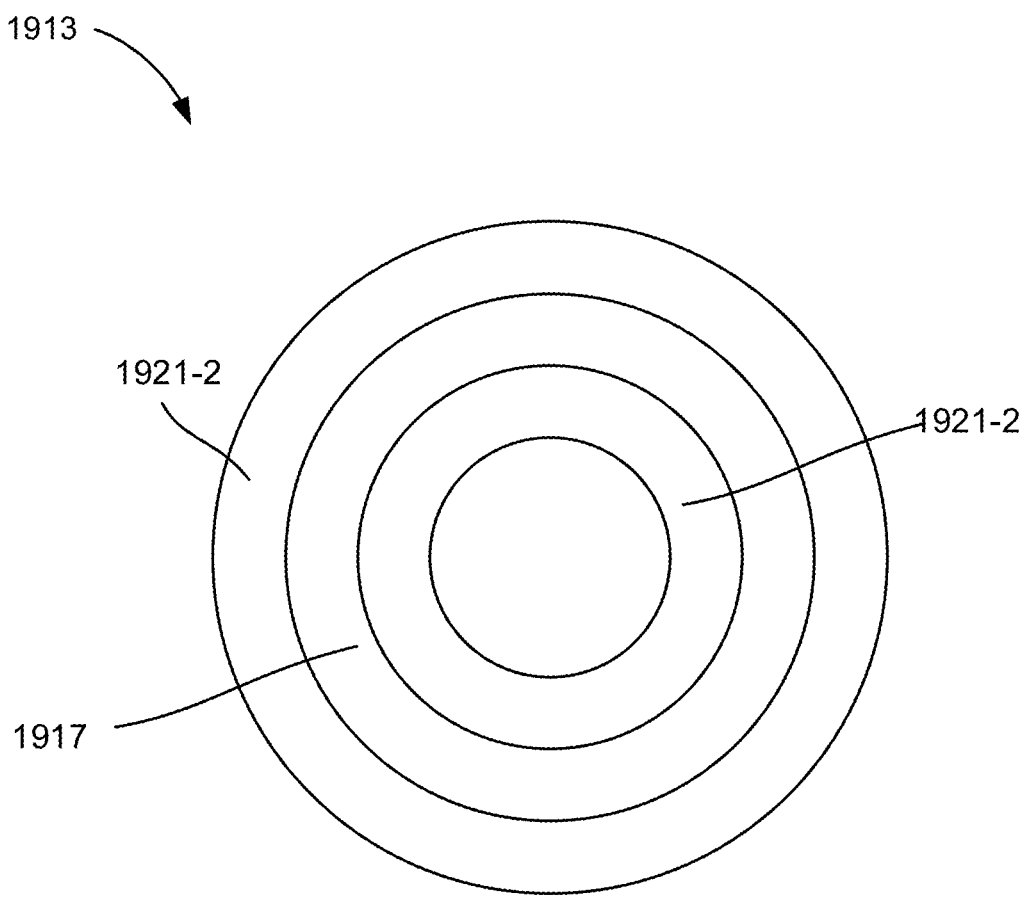
FIG. 19G is a bottom view of the piezoelectric element of FIG. 19F, according to an example of the principles described herein.

FIG. 19F is a schematic diagram of a piezoelectric element (1913), according to an example of the principles described herein. FIG. 19G shows a bottom view of the piezoelectric element (1913) according to an example of the principles described herein. As depicted, the piezoelectric element (1913) may include: a top electrode (1915), a first bottom electrode (1921-1); a second bottom electrode (1921-2); a piezoelectric layer (1917) disposed between the top and bottom electrodes; and three conductors (1919-1), (1919-2), and (1919-3) that are electrically coupled to the bottom and top electrodes (1915), (1921-1), and (1921-2), respectively. In the example depicted in FIG. 19F, each of the first and second bottom electrodes have an annular shape and the second bottom electrode (1921-2) surrounds the first bottom electrode (1921-1).

Figure 19H:
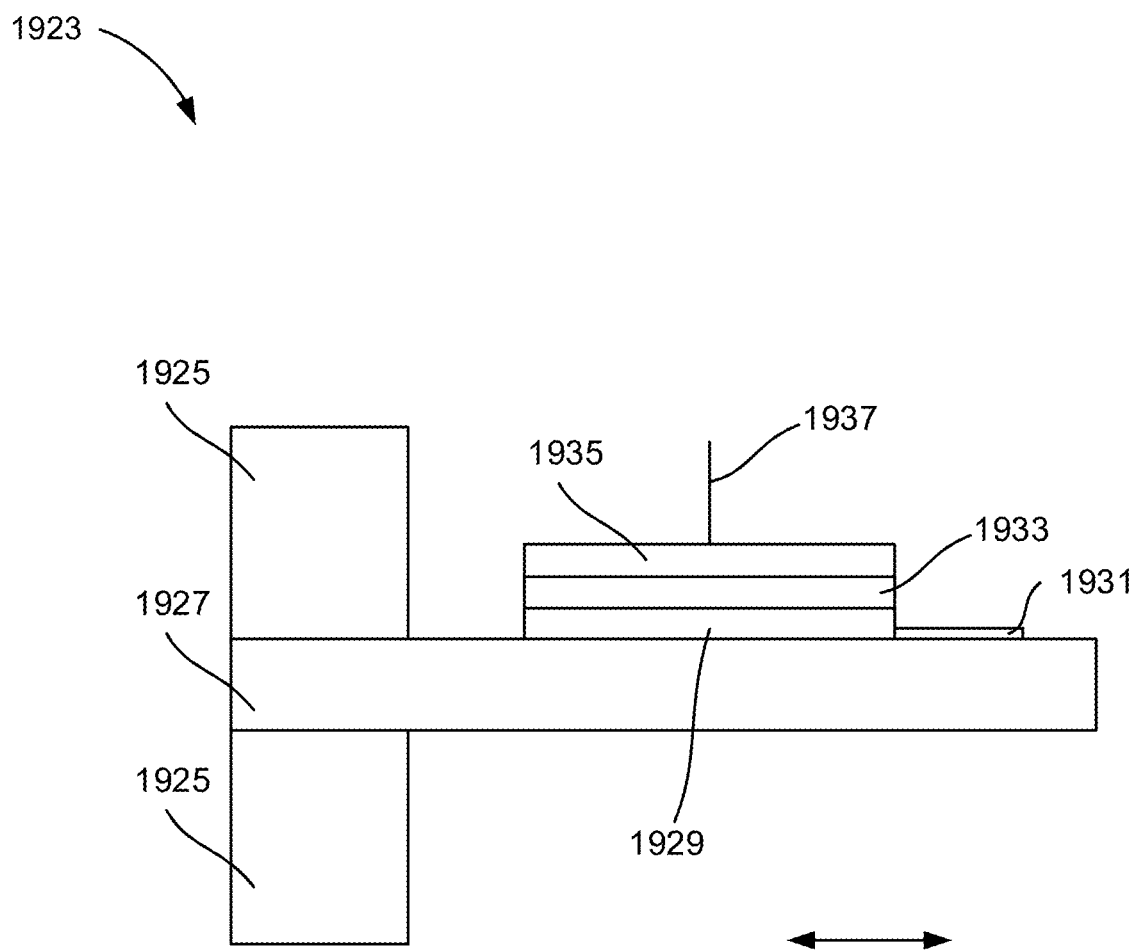
FIG. 19H is a cross sectional view of the piezoelectric element of FIG. 19F according to embodiments of the present disclosure.

FIG. 19H is a cross sectional view of the piezoelectric element (1923) of FIG. 19F according to an example of the principles described herein. As depicted, the piezoelectric element (1923) may utilize transverse mode of operation and include: a substrate (1925), a membrane (1927) secured to the substrate at one end; a bottom electrode (1929) that is electrically coupled to a conductor (1931); a piezoelectric layer (1933); and a top electrode (1935) that is electrically coupled to a conductor (1937). The membrane (1927) may be secured to the substrate (1925) at one end so as to vibrate in the transverse mode, as indicated by an arrow, i.e., the piezoelectric element may operate in the transverse mode. The membrane (1927) can be supported on both sides and is shown only on the left in FIG. 19H for simplicity.

It is noted that the piezoelectric element (1923) may have any suitable number of top electrodes. Also, it is noted that more than one piezoelectric element may be installed on the membrane (1927). It is further noted that the substrate (1925) and membrane (1927) may be formed of one monolithic body and the membrane is formed by etching the substrate.

Figure 20:
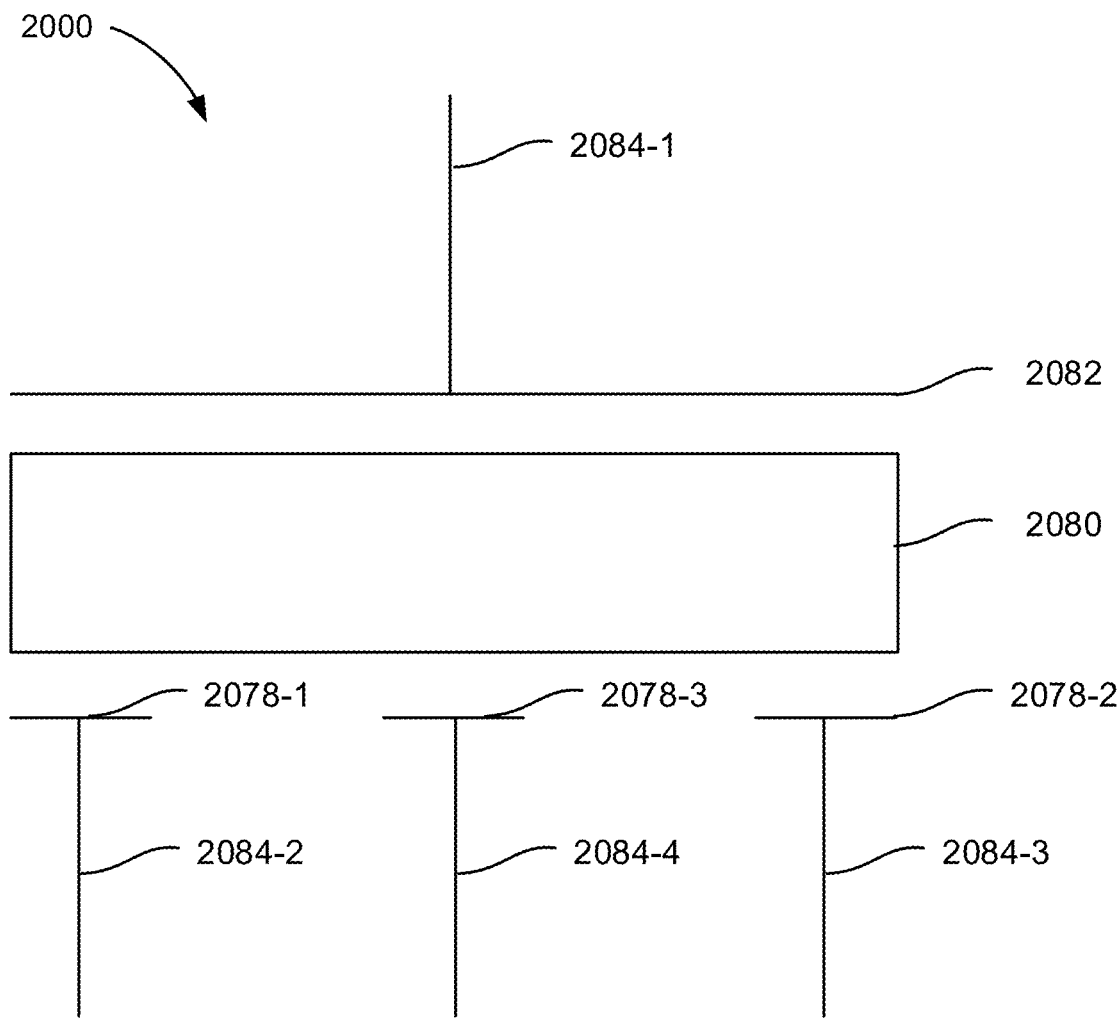
FIG. 20 is a schematic diagram of a piezoelectric element, according to another example of the principles described herein.

FIG. 20 is a schematic diagram of a piezoelectric element (2000), according to another example of the principles described herein. As depicted, an electrode (2082) may be disposed on the top surface of a piezoelectric layer (2080) and electrically connected to a conductor (2084-1) that may be connected to an electric circuit. Other conductors (2084-2), (2084-3), and (2084-4) may be connected to the bottom electrode (2078-1), (2078-2), and (2078-3), respectively. The electrode (2078-1), (2078-2), and (2078-3) may be disposed on the bottom surface of the piezoelectric layer (2080). In some examples, the piezoelectric element (2000) may be disposed on one membrane or three separate membranes.

Figure 21:
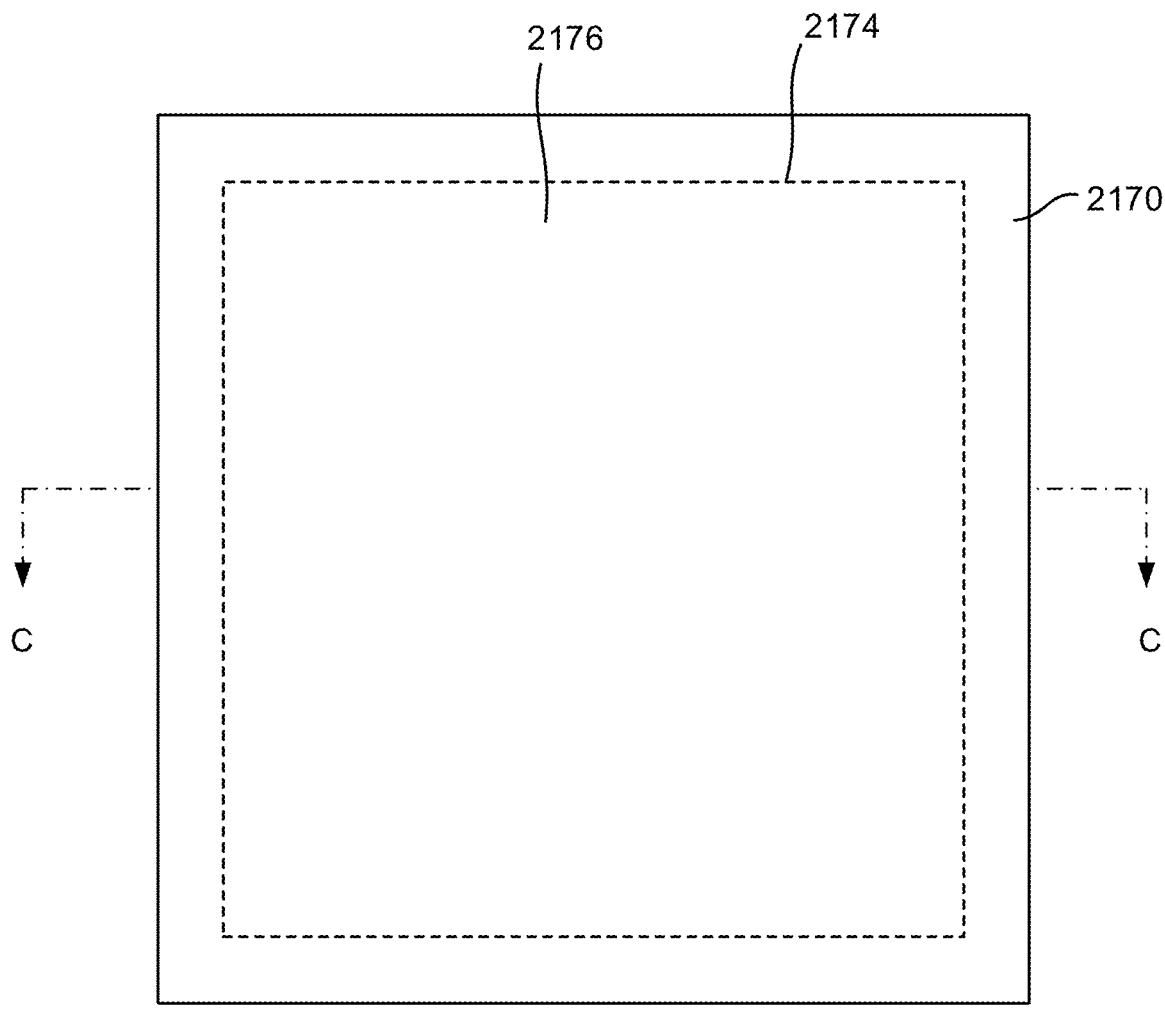
FIGS. 21-25 illustrate the fabrication of a piezoelectric element, according to an example of the principles described herein.
Figure 22:
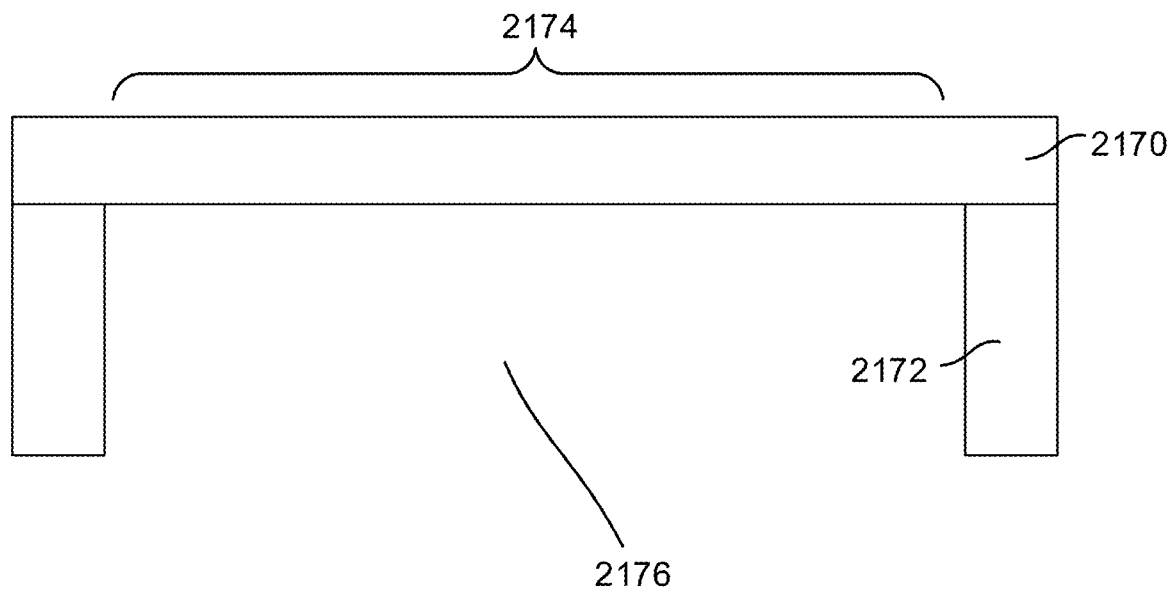

FIGS. 21-25 illustrate the fabrication of a piezoelectric element, according to an example of the principles described herein. FIG. 21 shows top view of a membrane (2174), which may be formed by forming a membrane layer (2170) on a substrate (2172), and forming a cavity (2176) in the substrate (2172). FIG. 22 shows a cross sectional view of the structure in FIG. 21, taken along the line C-C. In some examples, the membrane (2174) may be deposited by a suitable wafer processing technique.

Figure 23:
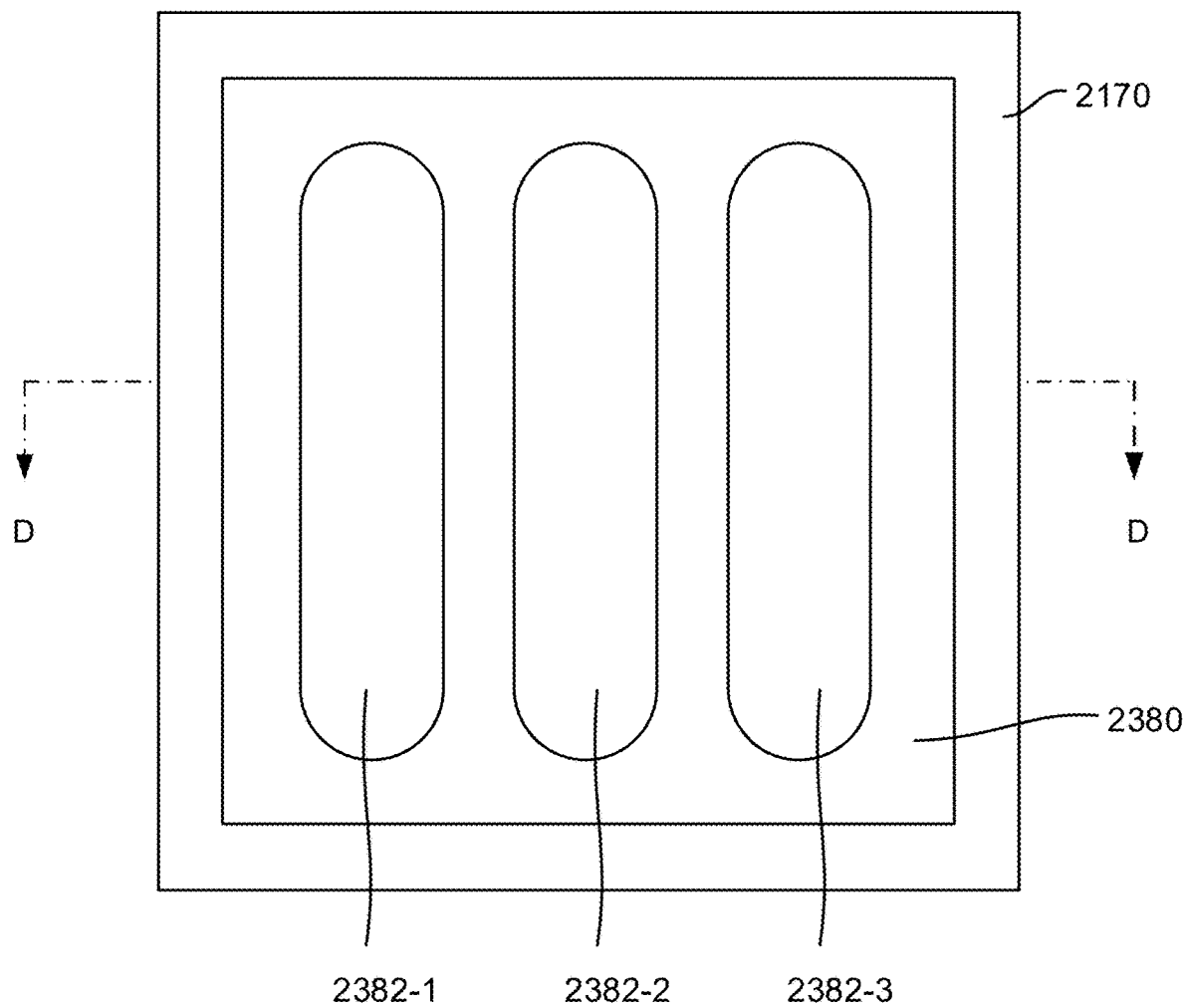
Figure 24:
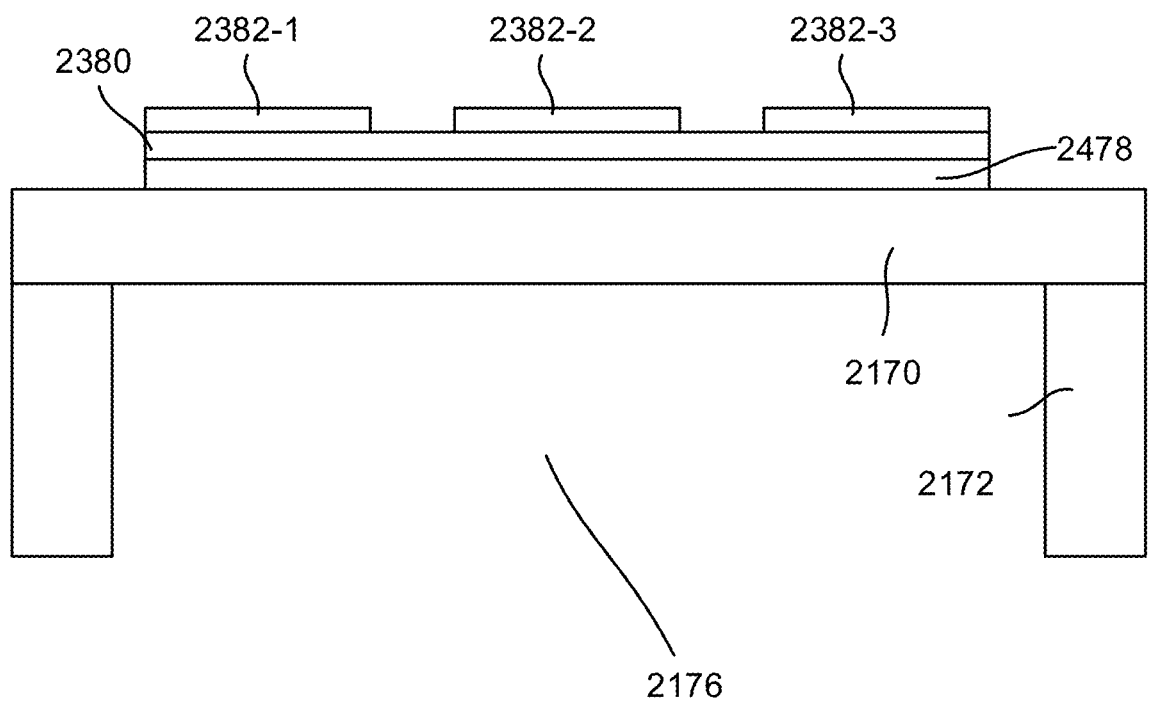

FIG. 23 shows a top view of a layer structure formed on the membrane layer (2170) and FIG. 24 shows a cross sectional view of the layer structure in FIG. 23, taken along the line D-D, according to examples of the principles described herein. As depicted, three top electrodes (2382-1, 2382-2, 2382-3), a piezoelectric layer (2380), and a bottom electrode (2478), may be formed on the membrane layer (2170). The top electrodes (2382-1, 2382-2, 2382-3), piezoelectric layer (2380), and bottom electrode (2478) may be deposited by suitable wafer processing techniques, such as deposition, sputtering, patterning and so on.

Figure 25:
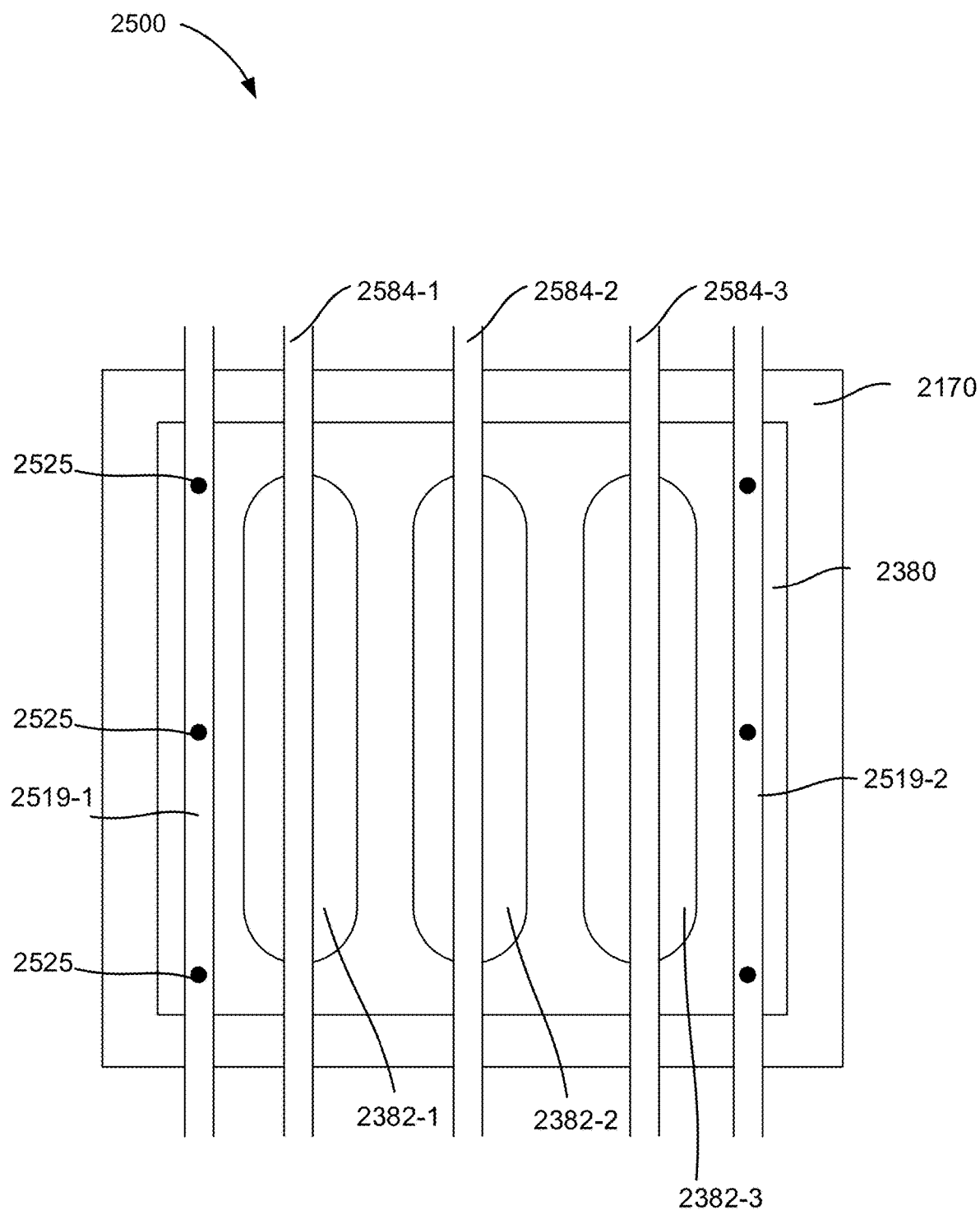

FIG. 25 shows a top view of a piezoelectric element (2500) according to an example of the principles described herein. As depicted, three conductors (2584-1), (2584-2), (2584-3) may be electrically coupled to the electrodes (2382-1), (2382-2), and (2382-3), respectively. Also, the conductors (2519-1) and (2519-2) may be electrically coupled to the bottom electrode (2478) through one or more vias (2525). In some examples, transmit drive and receive sensing is performed by connecting electronics to the bottom electrode (2478) through the vias (2525) and the conductors (2519-1, 2519-2). Each of the conductors (2584-1, 2584-2, 2584-3) may be connected to the ground or a DC bias voltage. The conductor (2584-2), may be connected to the ground or a first DC bias voltage, and the conductors (2584-1) and (2584-3) may be connected to the ground or a second DC bias voltage.

In summary, the present specification describes an imaging device that relies on PMUT-based transducers connected to control electronics on a per pixel basis and housed in a portable housing. The imaging device allows system configurability and adaptability in real time to actively control power consumption and temperature in the imaging device. This is done by minimizing power dissipation within the imaging device by 1) altering the number of channels and/or 2) actively controlling power dissipation in those channels such that temperatures within the imaging device do not exceed specification limits. All this is done while achieving superior performance than would otherwise be possible.

What is claimed is:

1. A method for selectively altering a plurality of channels of an imaging device, the method comprising:
receiving an indication to reduce power consumption at the imaging device, the imaging device comprising an array of piezoelectric micromachined ultrasonic transducers (pMUTs) connected to a plurality of transmit channels and a plurality of receive channels; and
in response to receiving the indication: (i) altering a state of at least one transmit channel of the plurality of transmit channels, the plurality of transmit channels being configured to cause the array of pMUTs to transmit a pressure wave; and/or (ii) altering a state of at least one receive channel of the plurality of receive channels, the plurality of receive channels being configured to process a reflection of the pressure wave received by the array of pMUTs.

2. The method of claim 1, wherein altering the state of the at least one transmit channel and/or the at least one receive channel comprises deactivating the at least one transmit channel and/or the at least one receive channel.

3. The method of claim 1, wherein altering the state of the at least one transmit channel and/or the at least one receive channel comprises reducing a power consumption level of the at least one transmit channel and/or the at least one receive channel.

4. The method of claim 1, wherein altering the state of the at least one transmit channel and/or the at least one receive channel comprises adjusting noise levels of a low noise amplifier (LNA), adjusting transmit voltage levels used by the pMUTs, and adjusting a plurality of elements used for transmission and reception.

5. The method of claim 1, wherein altering the state of the at least one transmit channel and/or the at least one receive channel comprises altering the state of the at least one transmit channel and/or the at least one receive channel for an entirety of an imaging cycle.

6. The method of claim 5, wherein the entirety of the imaging cycle comprises formation of an image scan line.

7. The method of claim 1, wherein altering the state of the at least one transmit channel and/or the at least one receive channel comprises altering the state of the at least one transmit channel and/or the at least one receive channel for a portion of the imaging cycle.

8. The method of claim 1, wherein the indication is an indication of a low-resolution imaging mode.

9. The method of claim 1, wherein the imaging device further comprises a temperature sensor configured to detect temperature of the imaging device, and the indication is an indication that a threshold temperature of the imaging device has been reached.

10. The method of claim 1, wherein the imaging device further comprises a battery configured to provide power to the imaging device, and the indication is an indication that a charge of the battery is low.

11. A method for selectively altering a plurality of channels of an imaging device comprising a battery configured to provide power to the imaging device, the method comprising:
receiving, at the imaging device, an indication that a charge of the battery is low; and
altering a state of at least one of a plurality of transmit channels and a plurality of receive channels based on the received indication.

12. The method of claim 11, wherein the indication is an indication to reduce power consumption, and altering the state of the at least one of the plurality of transmit channels and/or the plurality of receive channels comprises deactivating the plurality of transmit channels and the plurality of receive channels.

13. The method of claim 11, wherein the indication is an indication to reduce power consumption, and altering the state of the at least one of the plurality of transmit channels and/or the plurality of receive channels comprises reducing a power consumption level of the plurality of transmit channels and the plurality of receive channels.

14. The method of claim 11, wherein altering the state of the at least one of the plurality of transmit channels and/or the plurality of receive channels comprises adjusting noise levels of a low noise amplifier (LNA), adjusting transmit voltage levels used by piezoelectric micromachined ultrasonic transducers (pMUTs), and adjusting a plurality of elements used for transmission and reception.

15. The method of claim 11, wherein altering the state of the at least one transmit channel and/or the at least one receive channel comprises altering the state of the at least one transmit channel and/or the at least one receive channel for an entirety of an imaging cycle.

16. The method of claim 15, wherein the entirety of the imaging cycle comprises formation of an image scan line.

17. The method of claim 11, wherein altering the state of the at least one transmit channel and/or the at least one receive channel comprises altering the state of the at least one transmit channel and/or the at least one receive channel for a portion of the imaging cycle.

18. The method of claim 11, wherein the indication is an indication of a low-resolution imaging mode.

19. The method of claim 11, wherein the imaging device further comprises a temperature sensor configured to detect temperature of the imaging device, and the indication is an indication that a threshold temperature of the imaging device has been reached.

20. A method for selectively altering a plurality of channels of an imaging device, the method comprising:
   receiving an indication of a low-resolution imaging mode at the imaging device; and
   altering a state of at least one of a plurality of transmit channels and a plurality of receive channels based on the received indication.

* * * * *